United States Patent [19]

Vaillancourt

[11] Patent Number: 4,617,012

[45] Date of Patent: Oct. 14, 1986

[54] STERILE CONNECTOR WITH MOVABLE CONNECTION MEMBER

[75] Inventor: Vincent L. Vaillancourt, Livingston, N.J.

[73] Assignee: Manresa, Inc., Hillsdale, N.J.

[21] Appl. No.: 792,460

[22] Filed: Oct. 29, 1985

[51] Int. Cl.⁴ ............................................. A61M 5/00
[52] U.S. Cl. ...................................... 604/29; 604/283; 604/905; 285/12
[58] Field of Search ............. 604/29, 283, 905, 32–33, 604/248–249; 285/12

[56] References Cited

U.S. PATENT DOCUMENTS

| | | | |
|---|---|---|---|
| 4,256,106 | 3/1981 | Shoor | 604/905 |
| 4,334,551 | 6/1982 | Pfister | 604/905 |
| 4,338,933 | 7/1982 | Bayard et al. | 604/905 |
| 4,346,703 | 8/1982 | Dennehey et al. | 604/29 |
| 4,369,779 | 1/1983 | Spencer | 604/905 |
| 4,405,315 | 9/1983 | Handt | 604/29 |
| 4,432,766 | 2/1984 | Bellotti et al. | 604/283 |
| 4,452,473 | 6/1984 | Ruschke | 604/905 |
| 4,507,119 | 3/1985 | Spencer | 604/905 |
| 4,541,829 | 9/1985 | Munsch et al. | 604/29 |
| 4,557,727 | 12/1985 | Handt | 604/410 |

*Primary Examiner*—Dalton L. Truluck
*Assistant Examiner*—Michelle N. Lester
*Attorney, Agent, or Firm*—Ralph R. Roberts

[57] ABSTRACT

This connection apparatus shows two arrangements for receiving a connector assembly of effluent and influent halves, with this apparatus providing for the transfer and alignment of the connected halves. These assembled halves are brought to the apparatus and the halves are manipulated to effect separation, after which the effluent connector half is moved to bring the effluent connector half into alignment and axial coincidence with a new and sterile influent connector half. By and through manipulation, the halves are secured into a fluid-tight condition whereat the fluid may be caused to flow through the connected halves. In a first arrangement, the apparatus includes a sliding action, with the apparatus having a tongue-and-groove construction. The other arrangement utilizes a rotary action, with a disc-like member associated with a cup-like member. Relative movement of the two members is made to effect the transfer and alignment of the effluent and influent halves.

42 Claims, 54 Drawing Figures

{% endraw %}

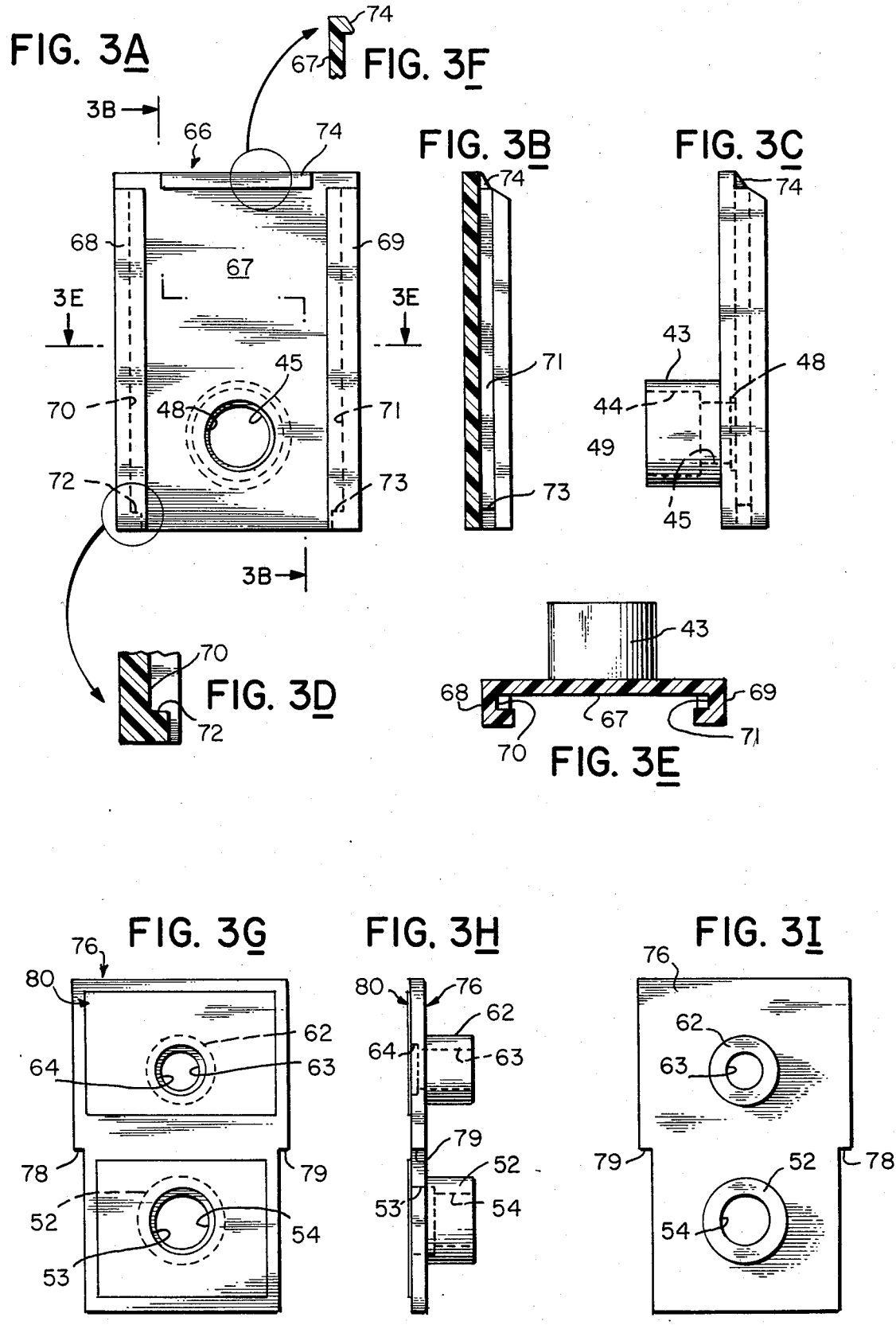

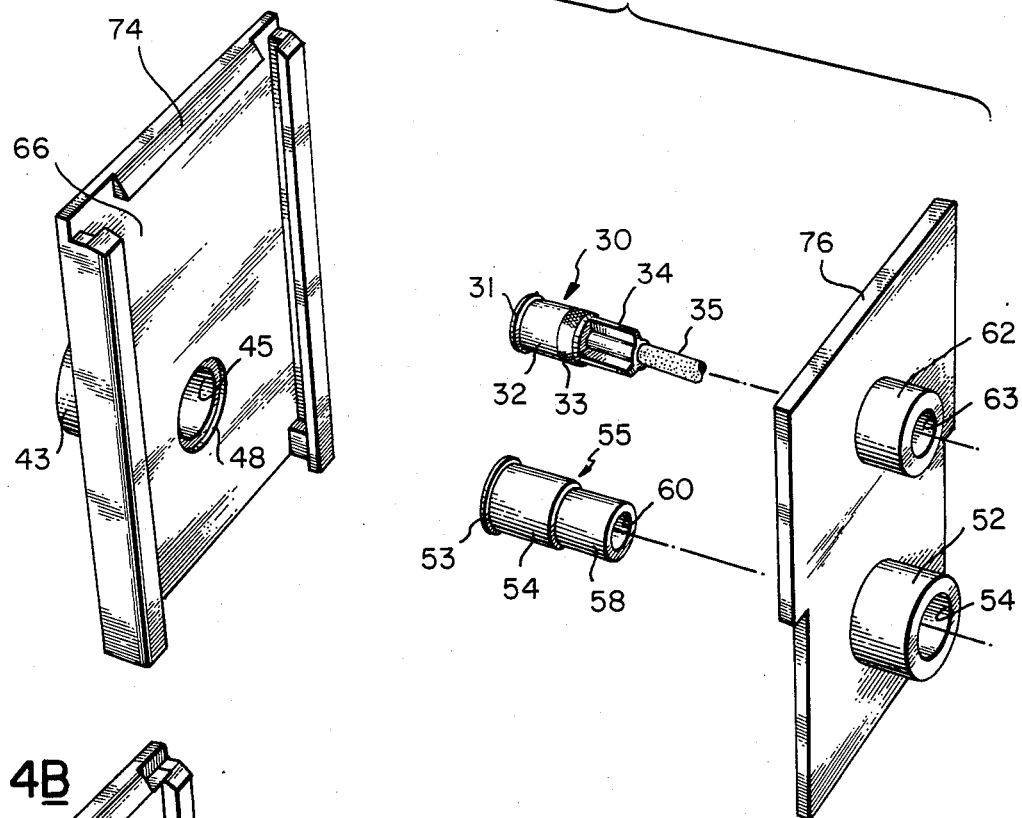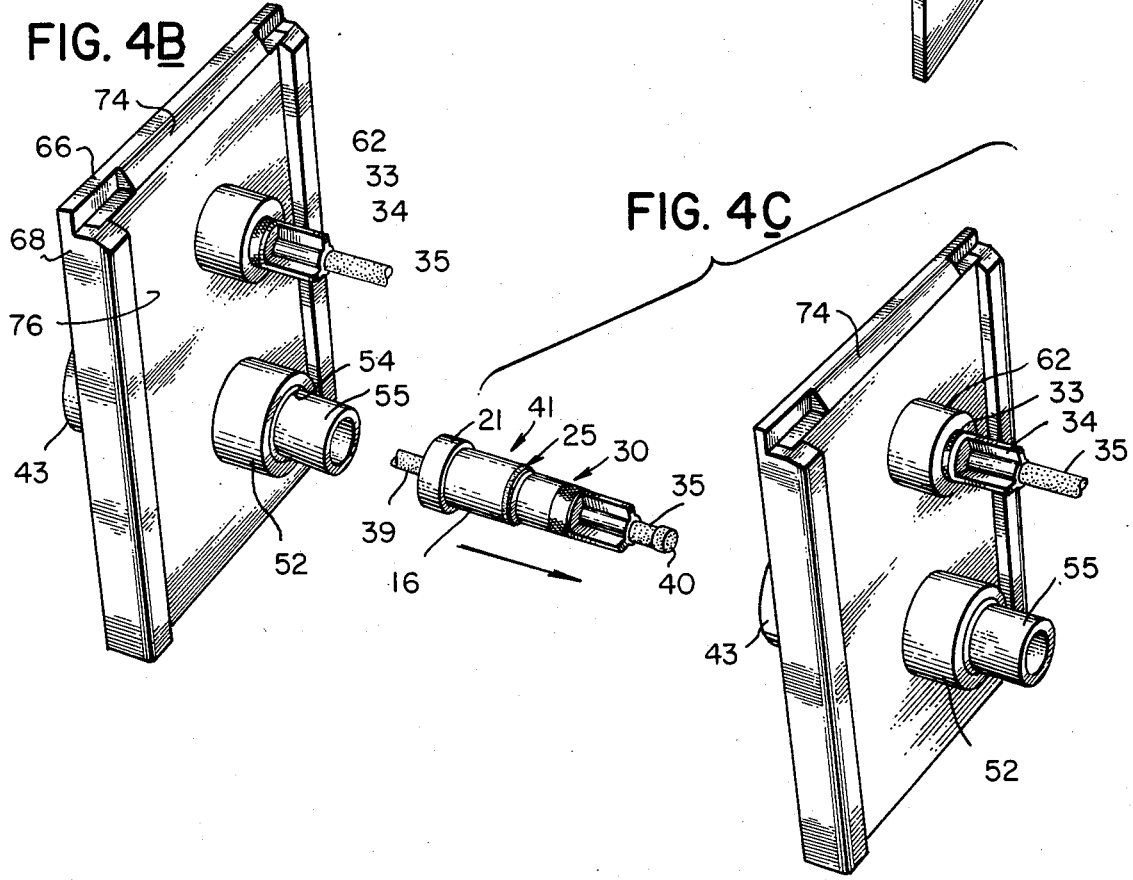

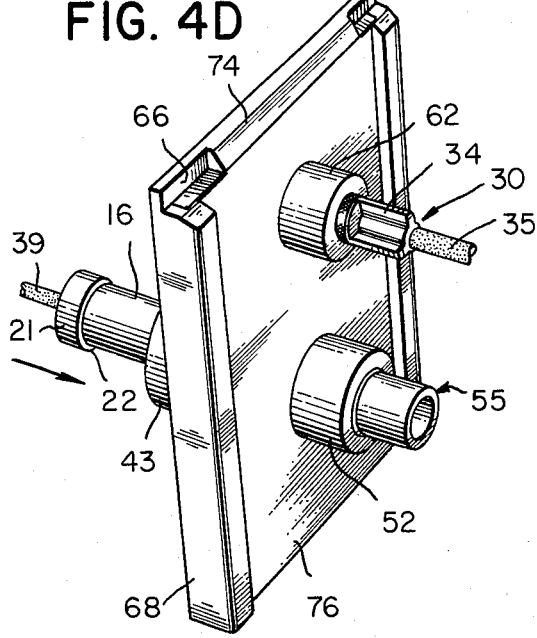
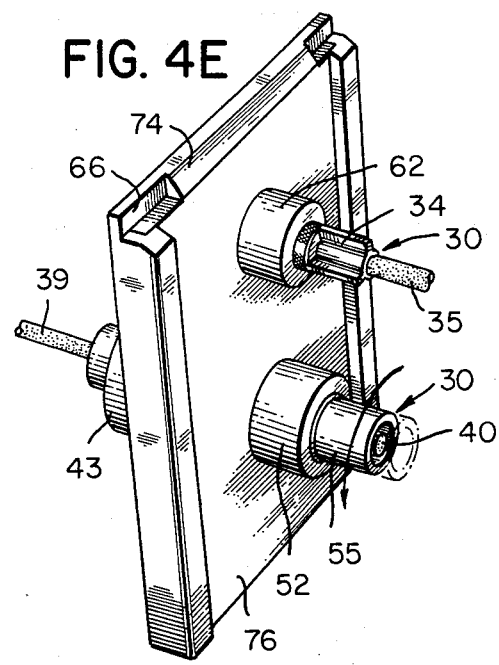
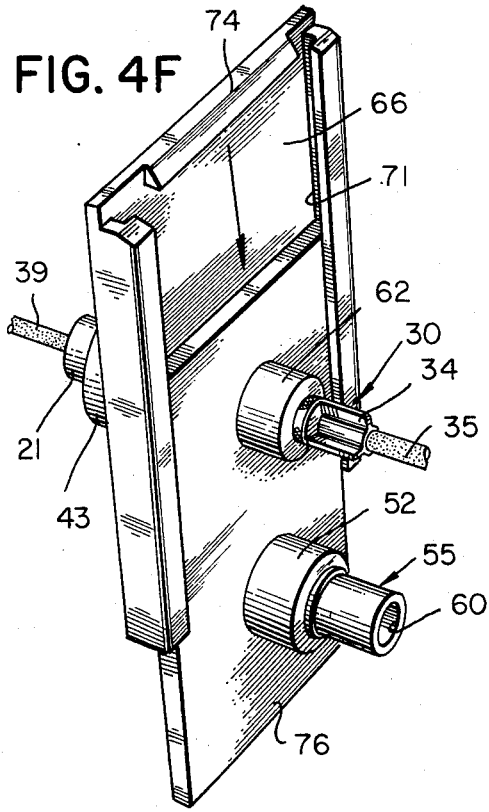
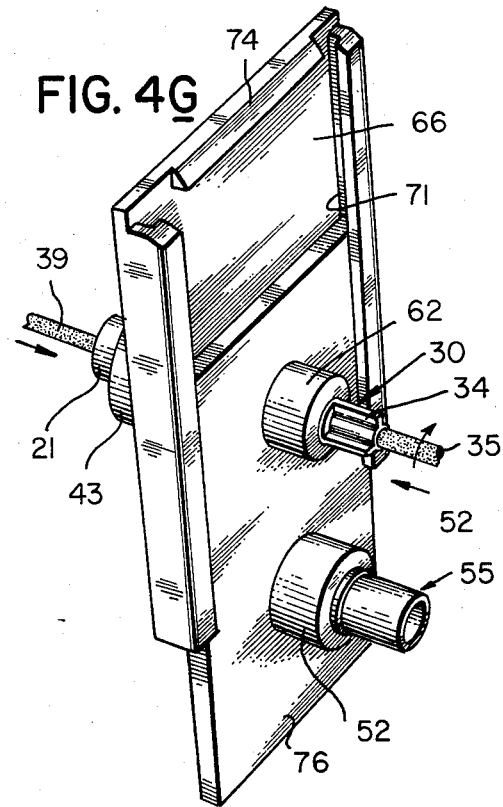

FIG. 9A
FIG. 9B
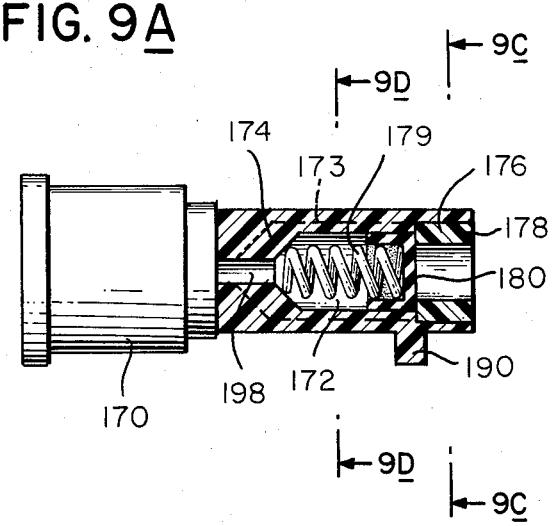
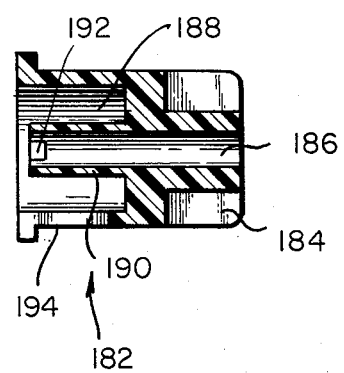
FIG. 9C
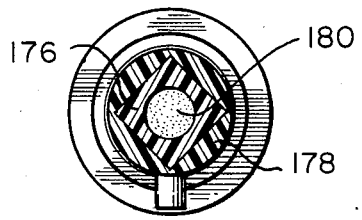
FIG. 9D
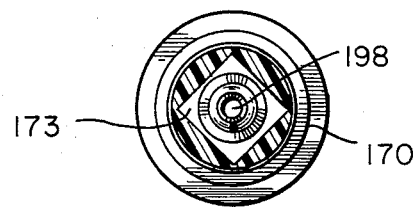
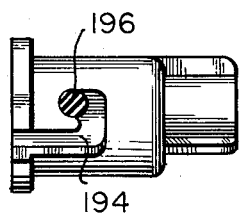
FIG. 9E

STERILE CONNECTOR WITH MOVABLE CONNECTION MEMBER

CROSS-REFERENCE TO RELATED APPLICATION

To the extent applicable, this invention is believed to be found in the same classification of art as in my U.S. Pat. No. 4,511,359, which issued on Apr. 16, 1985, and entitled "STERILE CONNECTION DEVICE."

BACKGROUND OF THE INVENTION

1. Field of the Invention

As established in and by the U.S. Patent Office, this invention is believed to be found in the classification of art directed to a sterile connector as applied for human and like use. This connector and package provides manipulation and a positive connection of a first half to an unused second half after a used second half is disconnected. Two embodiments are exemplified. One device uses a sliding actuation and one utilizes a movable ring.

2. Description of the Prior Art

A discussion of sterile connection devices has been made in the above-identified co-pending application, and additionally to be considered are U.S. Pat. Nos. 4,405,312 to GROSS et al, as issued Sept. 20, 1983; also known is 4,412,834 to KULIN et al, as issued Nov. 1, 1983; and 4,411,662 to PEARSON, as issued Oct. 25, 1983. All these patents show disengaging means or apparatus while proposing to insure sterility during operation. These showings require manipulation and, at times, the control leaves room for contamination from external conditions. The present invention provides a sterile connector package which is easily manipulated by an attendant and provides sterility at all times. This sterile connector package is relatively inexpensive and may be used by a patient for dialysis attachment or the like.

Coupling devices are well known and are particular to the field of use. Electrical connectors are widely used as are the connectors for fluid flow. The connector device of this invention is particularly used and useful for fluid flow in the field of medicine when and where sterility is to be maintained at the time of disconnect. Kidney deficiency or failure has led to the use of dialysis which requires repeated "hook-up" to the blood system or to the recently-adopted continuous ambulatory peritoneal dialysis. CAPD, "Continuous Ambulatory Peritoneal Dialysis," has been developed by the medical community and costs about one-half that of conventional dialysis. This CAPD is less traumatic to the body of the user, requires far less time and, more importantly, can be done at home. Under these circumstances, a sterile connecting device is especially important.

It is estimated that about fifty thousand people need dialysis treatment to live. CAPD uses a small, flexible catheter surgically implanted into the patient's abdominal cavity. A plastic bag containing the treating solution is attached to the catheter and through gravity this solution is fed through the catheter and into the bottom of said abdominal cavity. The emptied bag, although still attached, is now clamped and stored in the patient's pocket. The waste products in the blood are drawn by natural means into the solution. The impurity-laden fluid is then drained from the cavity into the bag which has now been placed on the floor. Although as many as four bags per day may be needed for cleansing the blood of a patient, the patient need but only half an hour to make each complete exchange and at the other times the patient is unencumbered. This exchange process is painless and the patient quickly becomes accustomed to the pressure of the dialysis fluid in the abdomen and in the use of this system.

A problem with this method and others using implanted catheters is the contamination developed by handling. It is essential that a sterile connector half as provided by the several embodiments of this invention insure that the catheter end be protected at the time of disconnection of the device.

SUMMARY OF THE INVENTION

This invention may be summarized, at least in part, with reference to its objects. It is an object of this invention to provide, and it does provide, a sterile connection device that employs a connection housing in which both influent and effluent connector portions are removably mounted and, by manipulation, separation of an initial connection half is achieved. The housing is manipulated for alignment of a new influent connector half with an effluent connector half and a manipulation is made to effect a new conductor path.

It is a further object of this invention to provide, and it does provide, a sterile connector assembly device that insures sterility before, during and after use. This assembly includes male and female halves arrayed in a carrier that provides means for disassembly of a first half of the connector from a second half and, while in a protected environment, the first half is moved to alignment with a new second connector half connected to a dialysis solution supply whereat a connection of the halves is made. This device provides exclusion of particles to and into the conducting passageway and also to the second half of the connector.

It is a further object of this invention to provide, and it does provide, a sterile connector assembly device which includes male and female halves carried and inserted into a tongue-and-groove apparatus particularly providing a mounting path in which a first connector assembly that has been used previously is separated by manipulation with that second connector half from the dialysis supply and now closed and severed as by a crimped clip. The first connector half is moved into position so a second, new connector half is in alignment with the first connector half and, in a protected manner, is caused to be tightened into a connected position.

In brief, this invention illustrates two manipulative housing concepts by and in which a connector device has separable halves. The device has a housing with movable means which enables the connector half (effluent) from the patient to be moved to and into alignment with a connector half (influent) attached to a bag supply of a dialysis solution. A sleeve is used to retain and enclose the removable influent half of the coupling which contains the used connection to a dialysis bag. The movable device portion is movable to bring the effluent and influent halves into alignment and, by manipulation, effect a connection.

There are two devices shown that insure an easy and positive disconnect procedure. In one device, a sliding motion is used to transfer the connector half from the patient to a new connector half from a dialysis treatment solution in a bag supply. Separation from the used connector half is achieved easily. Discarding of this used half of connection is a matter of choice.

In a first device, the manipulative housing includes a grooved half having a stop portion at the top of the grooves with molded stops at the other end of the grooves. A T-shaped member is movable in said grooves and has two boss portions, both with counterbores. One boss is adapted to retain, in a rotatable manner, an influent connector half within a sleeve. The sleeve is constructed to provide gripping means for retaining the second half of a connector and particularly the wing portions thereof.

The second device provides rotating manipulative means in which a disc-like member having securing means is rotatably moved in a cup-like housing. A sleeve has a rim portion sized so as to be carried in a shallow counterbore in the disc-like member. The shank portion of this sleeve extends through a bore and boss portion of the cup-like housing. The sleeve is adapted to receive and retain the influent used portion of the connector and is removed with a rotating action. After separation, the sleeve is moved into the boss portion of the cup-like member while the disc-like portion and cup-like portion are moved one hundred eighty degrees to each other to bring the influent and effluent halves into alignment, and connection is effected to provide a new fluid path from the dialysis bag to the patient.

In addition to the above summary, the following disclosure is detailed to insure adequacy and aid in understanding of the invention. This disclosure, however, is not intended to cover each new inventive concept no matter how it may later be disguised by variations in form or additions of further improvements. For this reason, there have been chosen specific embodiments of sterile connector assemblies as adopted for use for transferring fluids and showing a preferred means for constructing and using these connector assemblies. Thes specific embodiments have been chosen for the purposes of illustration and description as shown in the accompanying drawings wherein:

BRIEF DESCRIPTION OF THE DRAWINGS

FIG. 3A represents a face view of a retaining guide member and showing stops and grooved guideways for a mating member;

FIG. 3B represents a sectional side view of the member of FIG. 3A, this view taken on the line 3B—3B thereof and looking in the direction of the arrows;

FIG. 3C represents a side view of the guide member of FIG. 3A, this view looking from left to right of this guide member and showing in particular the boss extending from the back portion;

FIG. 3D represents a diagrammatic enlarged view, partly in section, of a stop molded in a groove of the guide member;

FIG. 3E represents a sectional view of the member of FIG. 3A, this view taken on the line 3E—3E thereof and looking in the direction of the arrows;

FIG. 3F represents a sectional view, quite fragmentary and partly diagrammatic, this view showing a molded-in-place upper stop providing a limit for movement of a reciprocated member;

FIG. 3G represents a face view of a plate-like T-shaped member that is compatible with and mountable in the grooves in the member of FIG. 3A;

FIG. 3H represents a side view of the plate-like member of FIG. 3G;

FIG. 3I represents a rear view of the plate-like member of FIG. 3G;

FIG. 4A represents an exploded isometric view of the several components providing the sliding device and particularly using the members of FIGS. 3A and 3G;

FIG. 4B represents an isometric view with the components of FIG. 4A assembled into condition for sliding transfer;

FIGS. 4C, 4D, 4E, 4F, 4G and 4H represent isometric views of the sliding device of FIG. 4A, illustrating further progressive stages of use from assembly to disconnect of the connector halves, thence to transfer and a reconnecting, the transfer and reconnection shown in FIGS. 4F and 4G and as used in FIG. 4H;

FIGS. 9A, 9B, 9C, 9D and 9E represent sectional and end views showing yet another alternate influent connector half with a shut-off capability.

In the following description and in the claims, carious details are identified by specific names for convenience. These names are intended to be generic in their application. Corresponding reference characters refer to like members throughout the several figures of the drawings.

The drawings accompanying, and forming part of, this specification disclose details of construction for the purpose of explanation, but structural details may be modified without departure from the concept and principles of the invention and the invention may be incorporated in other structural forms than shown.

EMBODIMENT OF FIG. 1A THROUGH FIG. 1I

Figure 1A:
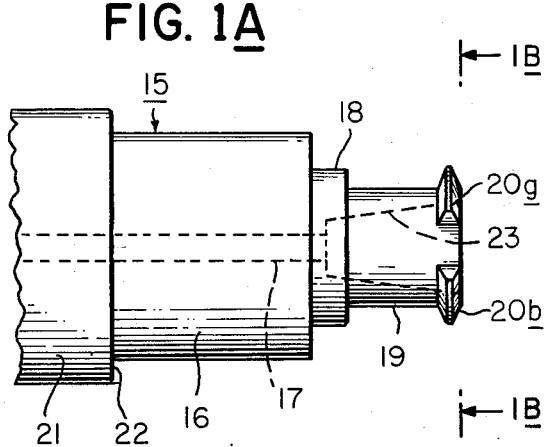
FIG. 1A represents a side view, partly diagrammatic, and in greatly enlarged scale, of a typical effluent connector half having thread portions for a luer lock configuration.

Connectors having two half portions are required in and by the two methods of transfer to be disclosed. Connectors may be of any selected arrangement, but in FIGS. 1A through 1I a locking connector is depicted. Alternate connector arrangements are disclosed hereinafter. No patentable distinction is ascribed to the connector arrangement. The depicted connector assembly is contemplated to be used in the depicted movable connector devices. This showing has an effluent connector half from the patient shown with an arrangement utilizing a luer lock connection commonly used with catheters, syringes and the like. In FIG. 1A, an effluent connector half, generally identified as 15, has a tubular body portion 16 and a central conductor path 17. The right end has a reduced diameter shoulder 18 and to the right is a stem portion 19 and at the end thereof is exemplified luer wing portions 20a and 20b. This connector half 15 is depicted with an enlarged left portion 21 on which is provided a stop shoulder 22. The central conductor path flows into or is connected to a tapered recess 23 formed in this effluent half. Luer lock connections to provide for fast connecting actuation usually have double-pitch threads and these lock wing portions 20a and 20b provide engagement for mating threads in the other connector half. The shoulder 18 is greater in diameter than the stem portion 19 and these sizes are compatible with a right influent connector half, to be described later.

Figure 1B:
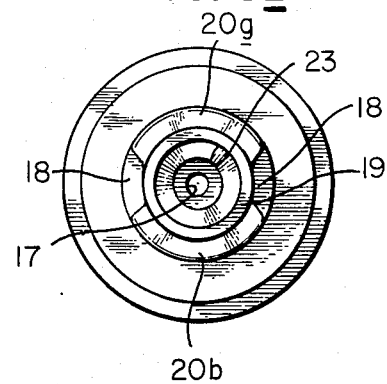
FIG. 1B represents a diagrammatic end view showing the thread end of FIG. 1A, this view taken on the line 1B—1B thereof and looking in the direction of the arrows.

In FIG. 1B, the threaded end 20 is shown as usually formed or provided with a luer lock connection. It is noted in this view that the threaded end member portion is formed with two leaf-like or wing portions, identified in this view as 20a and 20b. This configuration is well known in luer lock arrangements. This end view shows the relationship of the several components. It is to be noted that a luer connection uses mating tapered portions with a female cavity 23, as in the effluent connector mating, with a male plug-type tapered portion to be identified in FIG. 1F. When a lock is to be added to the device, threads are provided and as a fast disconnect is desired the double-pitch threads shown in this device are used.

Figure 1C:
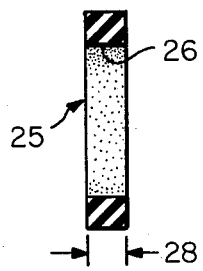
FIGS. 1C and 1D represent sectional side and plan or face views of a resilient washer used with the connector of FIG. 1A.
Figure 1D:
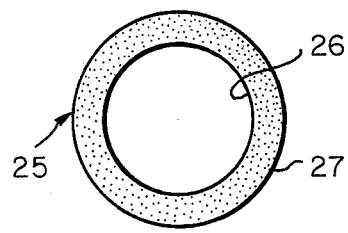

FIGS. 1C and 1D illustrate a resilient washer, generally identified as 25, having an aperture 26 and sized to be a snug retaining fit on the shoulder 18 of the effluent connector body half 16. Outer diameter 27 of the mounted washer is about the same as the exterior diameter of portion 16. The washer 25 may have a slightly greater width 28 than shoulder 18. When the effluent connector 15 with washer 25 mounted thereon is drawn into a locked condition with the influent connector half as in FIG. 1J, the washer 25 becomes slightly bulged because of the force applied. As reduced to practice, this squeezing of the resilient washer is only a few hundredths of an inch and insures that the luer lock thread area, which prevents accidental disengagement of the seal of the connector, is also sealed by the resilient washer 25.

Figure 1E:
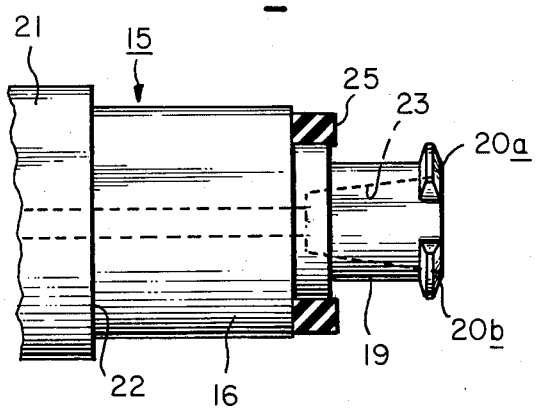
FIG. 1E represents a side view, partly in section, of the connector of FIG. 1A with the washer of FIG. 1C mounted thereon.

In FIG. 1E, the connector 15 of FIG. 1A is shown with washer 25 mounted on shoulder 18. It is to be noted that in mounted and non-engaged condition, the washer 25 is slightly wider than the shoulder 18, but other configurations may be made. The arrangement shown is a preferred embodiment.

Figure 1F:
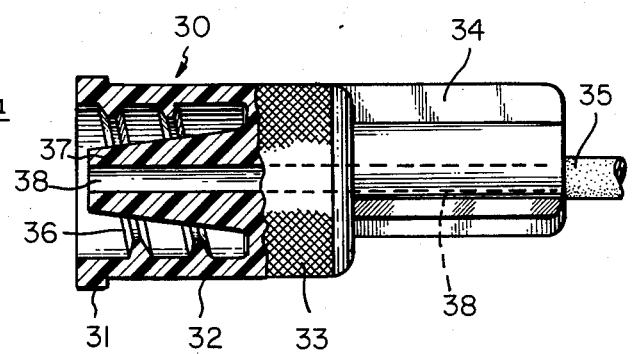
FIG. 1F represents a side view, partly in section, this view showing an influent connector half with a luer lock device and showing a tubular connection to a supply container, not shown.
Figure 1G:
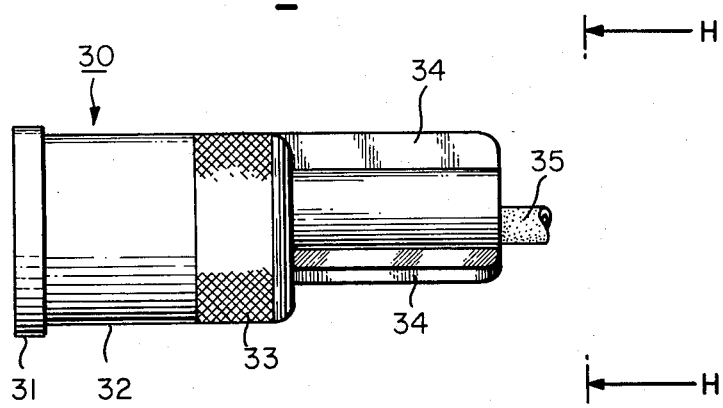
FIG. 1G represents a side view of the connector of FIG. 1F.
Figure 1H:
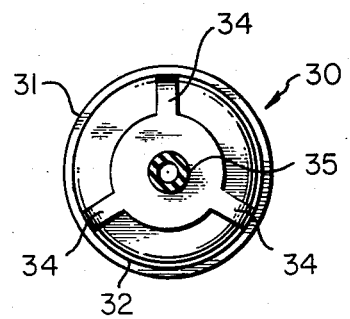
FIG. 1H represents an end view taken on the line 1H—1H of FIG. 1G and looking in the direction of the arrows.

In FIGS. 1F, 1G and 1H, an influent connector half of plastic (molded) is generally identified as 30 and is shown with a stop ring or flange 31 which is not greater in diameter than washer 25. The molded portion of plastic is depicted with a smooth portion 32, thence a knurled portion 33. This portion to the right of flange 31 is integral with a winged end 34 which provides positive engagement with a sleeve to be described hereinafter. Within this connector half is mounted and secured a flexible tubing 35. As shown, there are three wings or flutes 34, but there may be as few as two and, of course, more than three. It is to be noted that wings or flutes 34 are provided for turning insurance, but are not essential to achieve security as the knurl 33 can be and is used for assembly and disassembly of the connector halves. The interior of this connector half is formed with a threaded portion 36 which mates with the luer lock wing portions 20a and 20b of the effluent connector. A tapered male luer portion 37 provides the fluid-tight connection with female luer tapered socket 23. Within this tapered portion 37 is a fluid conduit 38 which connects to a flexible conductor or tube 35. As assembled for use, the connector halves 15 and 30 are also shown in reduced scale between FIGS. 4B and 4C. The effluent fluid from and to the patient to connector half 15 is shown as carried in a flexible tubular conductor 39. The tubing conductor 35 is shown as closed and then cut, and a grommet 40 is indicated as providing the means of closing the conductor 35. The length of tubing conductor 35 and the use and placement of grommet 40 are merely a matter of preference. The effluent from the patient is preferably collected in a containing member (not shown) and, after all or substantially all fluid has been drained from the patient, it is desirable that the connector 35 be severed to permit the patient to resume mobility and also to allow a new sterile connector with the movable connection member to be used. In an assembled condition as in FIG. 1I, the tapered portion 37 enters the tapered socket 23 and, with rotative tightening, the luer lock provides a fluid-tight connection. The resilient washer 25 is engaged by the left end of influent connector 30 to provide an air seal of the external portions. This washer 25 also provides with the luer lock a connection aid for maintaining integrity of the flow stream and an exclusion of external contaminants.

Figure 1I:
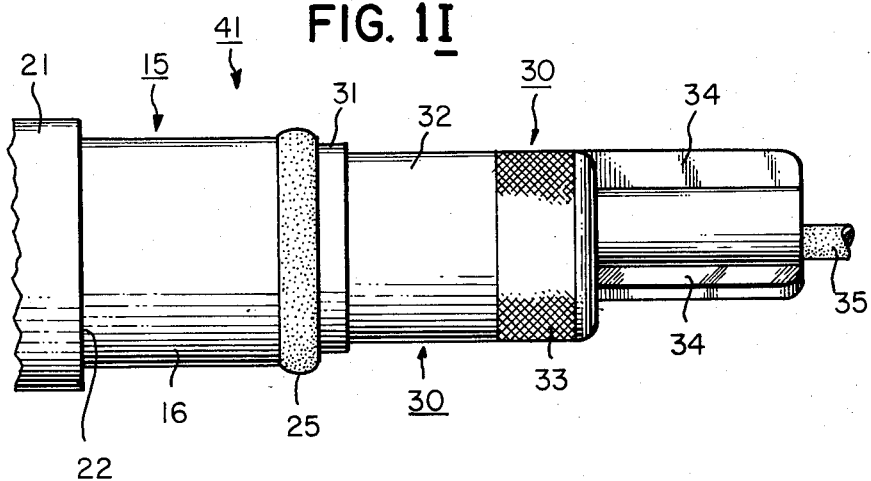
FIG. 1I represents a side view, partly diagrammatic, and showing the connector halves in an assembled condition for use with transfer apparatus.

In FIG. 1I, the connector havles 15 and 30 are shown in an assembled condition, with washer 25 slightly bulged through the squeezing produced when portion 16 is brought adjacent flange portion 31 and the two portions are tightened to a seating and retaining condition. This assembly is generally identified as 41. As viewed, the effluent half 15 is secured to the influent half 30, with the flexible tubing 35 extending from the connector half. Before being brought to the transfer device, the tubing 35 is usually bent on itself, cut, and a grommet 40 (FIG. 4C) applied thereto as by crimping to effect the closure as described above. The grommet when applied insures the fluid path from the patient is not invaded and non-contamination of this fluid path is maintained. This assembly of the connectors is seen and described in conjunction with FIG. 4C to be described hereinafter.

EMBODIMENT OF FIGS. 2A THROUGH 2F

Figure 2A:
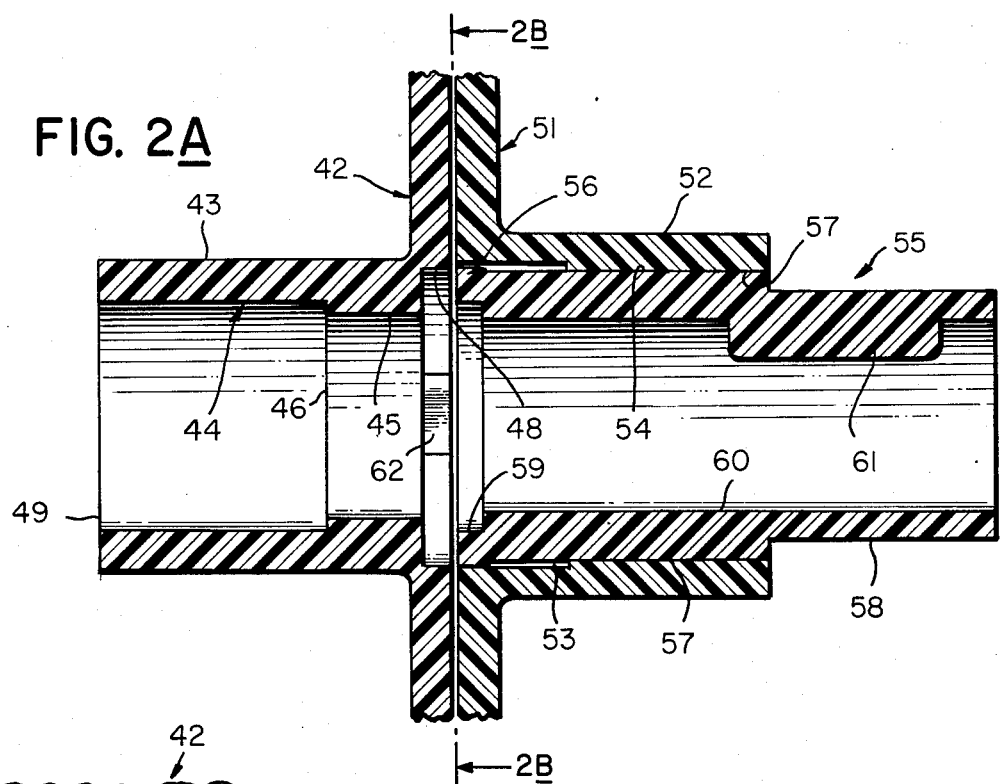
FIG. 2A represents a side sectional view of a movable transfer apparatus in the scale of FIG. 1A, this view partly diagrammatic and showing the relationship of the two portions of the transfer apparatus and a manipulative sleeve used therewith.

In the two devices for sterile connector transfer, a sleeve component is used with each device. In this depiction or showing, the molded members are shown in a slightly separated condition, but in practice these molded halves are substantially contiguous to provide exclusion of air from the outside. In the slide device as shown in detail in the showing of FIG. 4A through FIG. 4H, there is provided sealing means for excluding outside air from passing into the bore portions. A similar means is provided in and with the rotary device used in FIGS. 7A through 7F. As a slide device in which step-by-step operations are described and shown in conjunction with FIGS. 4A through 4H, the use of the sleeve is shown. In FIG. 2A, the left member, which is contemplated to receive the effluent connector half 15, is slideably retained in a plastic molded housing member, generally identified as 42. A boss 43 is formed with a bore 44 which is a slide fit for the effluent connector body 16, not shown, but exemplified in FIG. 1I. The bulged washer 25 is a friction fit in said bore 44. A reduced diameter portion 45 is sized to slideably pass flange 31 of the influent connector 30. This reduced diameter portion, although providing a shoulder 46, is not a stop and may if desired be chamfered or rounded so as to not impede the advancement of the assembled connector. This reduced bore 44 terminates at a shallow counterbore 48, to be more fully described in conjunction with FIG. 2B. This counterbore in actuality is only a few thousandths of an inch in depth. A stop shoulder 49 is formed at the left end of boss 43 and is spaced from the right face of member 42 so as to engage and provide a stop in way of shoulder 22 formed on connector half 15. It is to be noted that although portion 16 is slideable in bore 44, the bulged washer 25 extends outwardly sufficiently to provide the desired friction fit and also the desired exclusion of air.

The other half of the sliding device is also a plastic molding, which is generally identified as 51. A boss portion 52 integrally formed with and as a portion of a molding 51 has a stepped, through bore. The larger bore portion 53 is the same or about the same diameter as counterbore 48 formed in the left half 42 and, as reduced to practice, provides means for rotative and rightward and leftward movement of a sleeve, to be described hereinafter. The smaller bore of the stepped bore is identified as 54 and provides a sliding fit for the sleeve 55 to be used therein.

Sleeve 55 is depicted as a tubular molding and has a small exterior shoulder or flange portion 56 sized to be a sliding fit in the bore 53 and is stopped from rightward movement by the shoulder provided at the reduced diameter bore 54 in boss 52. The rest of the exterior of sleeve 55 has a reduced diameter 57 which provides a slide and rotating fit in bore 54 in boss 52. This sleeve, as shown, may have another reduced diameter portion 58 at its right end, but the size and extent of this portion are only a matter of design preference. A shallow bore 59 is sized to accept the shoulder 31 of connector 30 shown in FIG. 1F. This sleeve is also designed to receive the remainder of influent connector 30 as seen in FIG. 1F, with the outer diameter 32 and knurled portion 33 sized to be retained with this sleeve. A through bore 60 is sized to removably retain the smooth diameter 32 and to tightly engage the knurled portion 33 of the connector 30. Preferably, the sleeve is made of a length sufficient to retain and engage the flutes 34 of connector 30 (FIG. 1F) so a plurality of inwardly-extending, flute-engaging wings 61 are disposed to engage these flutes 34 of the connector 30.

Figure 2B:
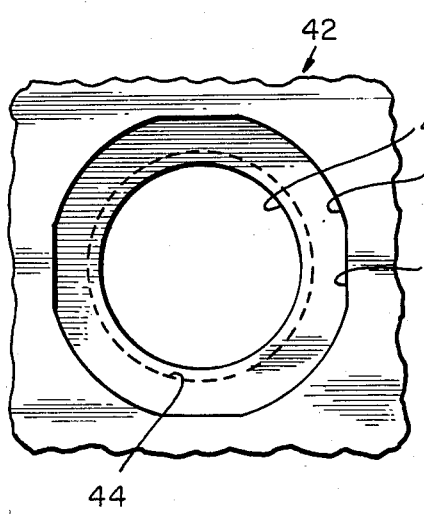
FIG. 2B represents a diagrammatic plan or face view showing a counterbore sized for retaining the sleeve and formed with shallow flats to provide releaseable retaining of the sleeve, this view taken on the line 2B—2B of FIG. 2A and looking in the direction of the arrows.

FIG. 2B depicts a means for removably retaining the flanged-end portion 56 of sleeve 55. As shown, the shallowing counterbore 48 is formed with a plurality of flats 61a which are sufficiently formed on the core pin to provide retaining means for retaining the sleeve 55 in the assembly of the transfer unit. Rather than flats 61a, small, inwardly-extending V-shaped ribs may be provided. Whatever the form or means, it is only sufficient to frictionally retain the sleeve during assembly. This localized retaining assist also accommodates small manufacturing tolerances that arise in molding procedures caused by temperature and material variations.

Figure 2C:
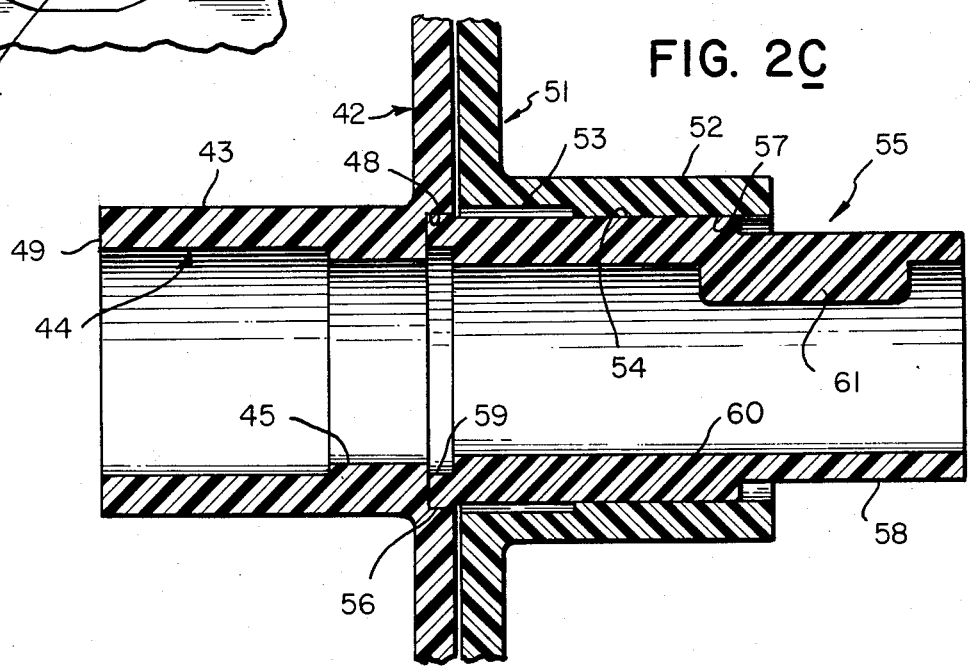
FIG. 2C represents the sectional side view of FIG. 2A, but with the sleeve mounted in the shallow counterbore in the left member portion and particularly seen in FIG. 2B.

FIG. 2C shows the side view of FIG. 2A, but with the sleeve 55 moved into the shallow counterbore 48 formed in member half 42. This positioning and placement of the sleeve 55 in this counterbore insures the placement and inserting action of the connector, as to be later discussed in connection with FIGS. 4C and 4D.

Figure 2D:
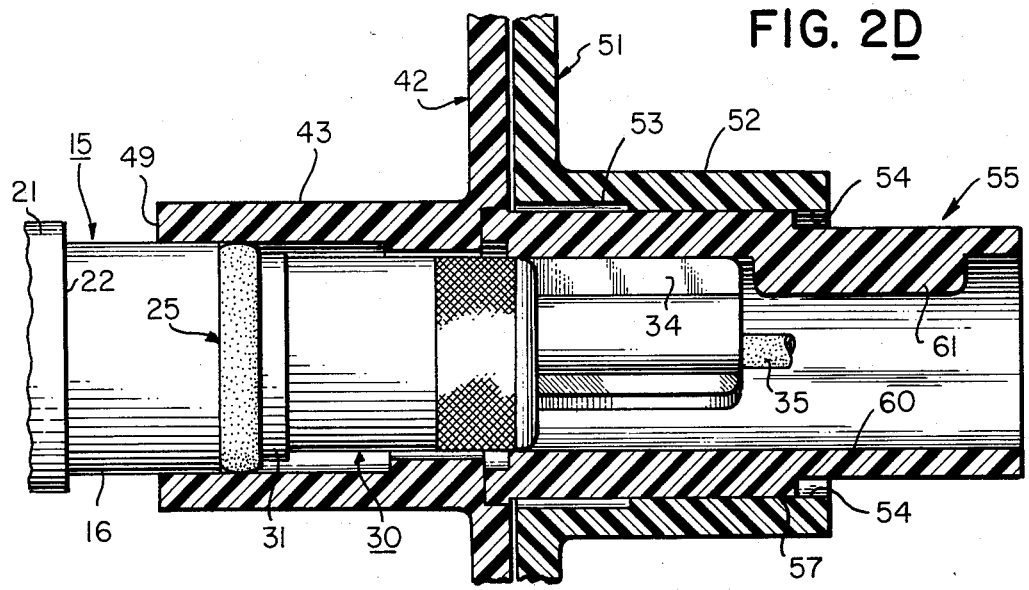
FIG. 2D represents the diagrammatic sectional side view of FIG. 2C, but showing a connector assembly partially inserted so that the flutes of the influent connector are in the sleeve and are just to the left of flute-engaging and -retaining portion of the sleeve.

FIG. 2D shows the side view of FIG. 2C, but with an assembled connector 41 (FIG. 1I) which is also shown with several components. This assembled connector 41 is connected to the patient by flexible tubing 39 (FIG. 4C), not shown in this view. The connector is inserted with tubing 35 closed, preferably by a grommet 40, as also seen in FIG. 4C. In this view, the connector 30 has just entered the sleeve 55. Flutes 34 of the connector 30 have come in way of the compatible portions 61 formed in the sleeve 55.

Figure 2E:
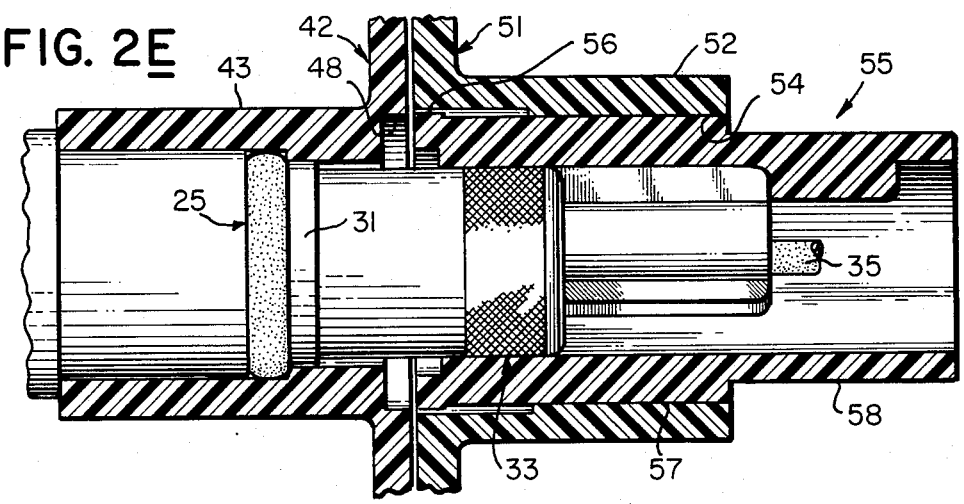
FIG. 2E represents the diagrammatic section side view of FIG. 2D, but with the assembled connector fully inserted into the sleeve, this view showing the sleeve moved for the shallow counterbore and with the flutes of the connector engaged by the flute-engaging portion of the sleeve, the stop shoulder of the effluent connector advanced into engaging condition with a left shoulder on the boss portion of the transfer apparatus.

FIG. 2E shows the connector assembly 41 moved rightwardly until stop shoulder 22 on the connector 15 engages and is stopped by the shoulder 49 on boss 43. The resilient washer 25 provides a friction fit in bore 44. The influent connector half 30 and the knurl portion 33 of connector 30 provide a friction fit in bore 60 in sleeve 55 so that said sleeve 55 may be or has moved slightly to the right. At this time, manipulation of the sleeve 55 or the connector assembly may be required to cause flutes 34 to slide by and alongside inwardly-projecting portions 61.

Figure 2F:
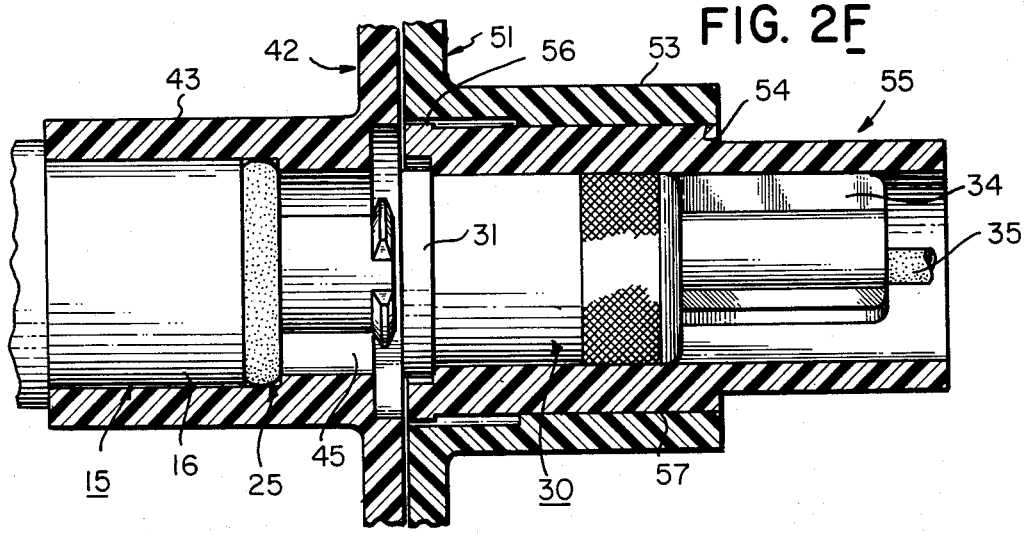
FIG. 2F represents the diagrammatic sectional side view of FIG. 2E, this representation showing the sleeve being rotated sufficiently for a disconnection of the effluent and influent halves as by a disconnection of the threads.

FIG. 2F shows the connector halves in a separated condition from the position of FIG. 2E. Rotation of sleeve 55 is performed with one hand while the effluent connector half 15 is held by the patient's other hand and maintaining shoulder 22 against end 49, as seen in FIG. 2E. It is noted that the thread-engaging wings at the right end of the connector 15 are shown as separated from connector 30, but this is only for illustrative purposes as when disconnect is achieved the connector 30 partially covers the right end of connector 15. The amount of overlap or telescope arrangement is determined by the termination of threads 38 within the connector 30 (FIG. 1F). Complete disengagement is achieved with further rightward movement of the sleeve 55.

Figure 2G:
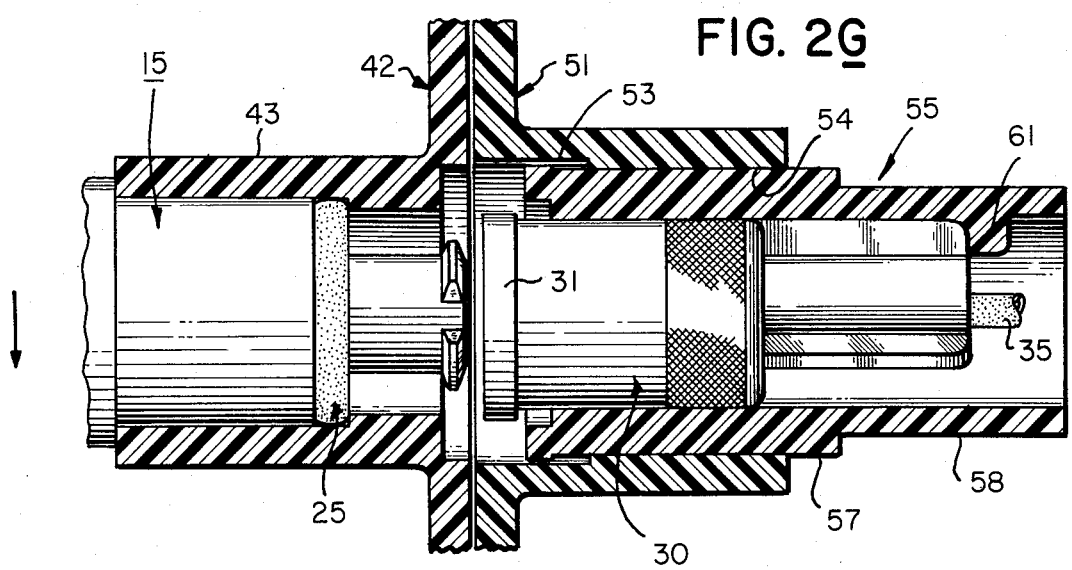
FIG. 2G represents the diagrammatic sectional side view of FIG. 2F, with the sleeve moved rightward sufficiently to move the influent connector from in way of a transfer actuation.

FIG. 2G illustrates the separation of the connector halves 15 and 30 and with the sleeve 55 further moved to the right so as to insure that a retained used connector 30 with tubing 35 closed by a grommet 40 is positively moved from in way of transfer movement of the members 42 and 51. This transfer movement is as shown in FIG. 4F.

Figure 2H:
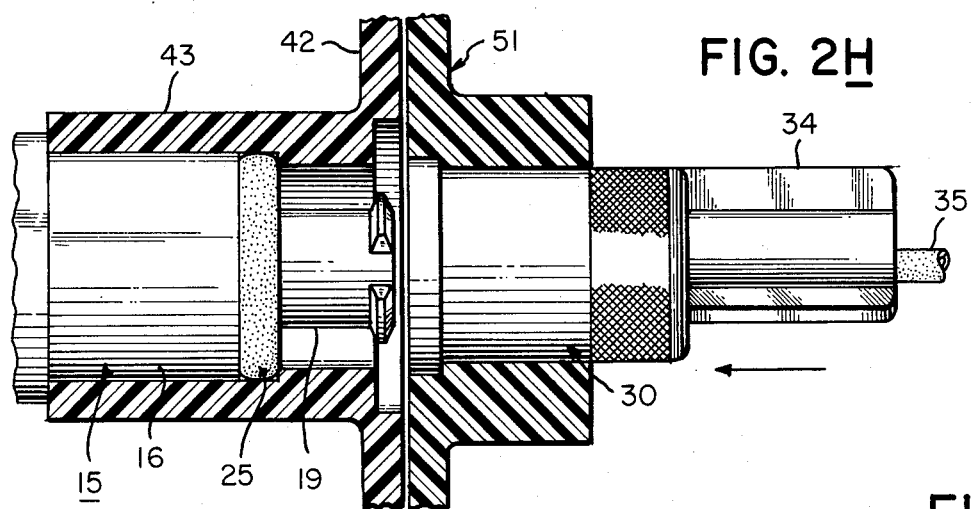
FIG. 2H represents a diagrammatic side sectional view and showing the effluent connector half moved to a position in way of a sterile influent connector half as connected to a fluid supply.

FIG. 2H illustrates the placement of the transferred connector 15 in alignment with a new sterile connector half 30 connected by tubing 35 to a fluid dialysis supply, not shown, and noted in later discussed FIGS. Conventionally, this fluid supply is in a bag and the length of tubing is usually more than five feet, but this length is not critical. For the purpose of identification, a hub 62 is provided in member 51 and has a bore 63 which is a sliding fit with the smaller barrel portions 32 and 33 of the connector 30. A shallow counterbore 64 is sized to removably retain the flange 31 of said connector 30. This is merely for the purpose of identification and specific showings in the preferred embodiments have other numbers applied to these specific members.

Figure 2I:
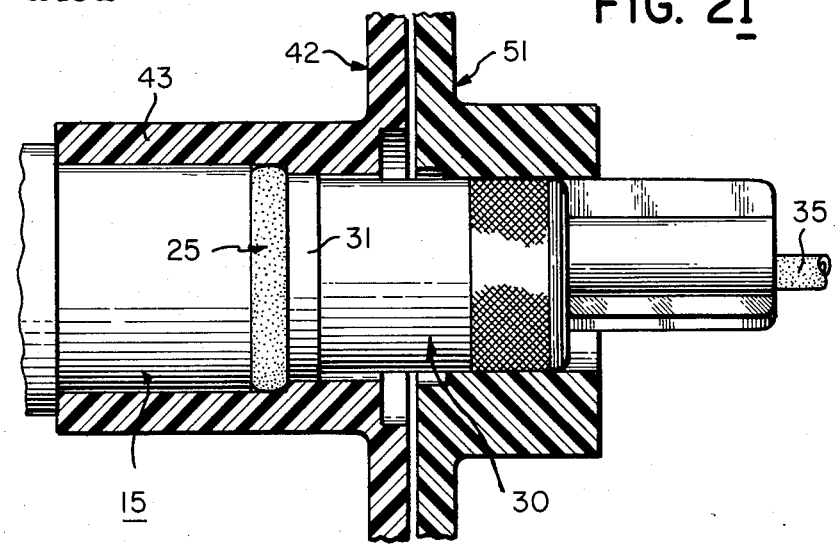
FIG. 2I represents the diagrammatic sectional view similar to FIG. 2H, but with the connector halves now in connected condition.

FIG. 2I exemplifies the connector 30 attached to connector 15. The required screwing motion is usually by the patient grasping the flutes 35 while connector 15 is retained in a fixed condition.

It is to be noted that FIGS. 2A through 2I are merely of the preferred construction and specific air exclusion means is not shown. These FIGS. are depicted with a small space in between and this is only for the purpose of illustration. There are depicted two devices for the insertion, disconnection, transfer and reconnection of connector halves and both are basically with a sleeve member and manipulation. Alternations of design for ease of manufacture of customer requirements are contemplated. The showing in FIGS. 2A through 2I is illustrative of the operations to be performed and specific application will be applied in the slide and rotary apparatus to be shown and described hereinafter.

EMBODIMENT OF FIGS. 3A THROUGH 3I

A first embodiment providing sliding transfer is made using the device of FIGS. 3A through 3I. In FIGS. 2A through 2I, the operation of the members 42 and 51 is shown in an illustrative sense, but in this embodiment of and for reciprocative movement the components are separately identified. In FIG. 3A is depicted a retaining guide which is one of the members that provide the slide transfer apparatus for the sterile connector. A grooved receiving member 66 is shown having a generally rectangular configuration, and from a back portion 67 there extends forwardly groove-retaining integral portions 68 and 69 and which said rectangular grooves 70 and 71 are formed by die-mold means. At the lower end of each groove there are provided integrally-formed stop portions 72 and 73. These stops 72 and 73 are less than the depth of the grooves so that a mating slide member as shown in FIGS. 3G, H and I has the longitudinal edge portions guided and retained in the grooves 70 and 71. The mating slide member in a transfer position and condition has a substantial portion not in the grooves as discussed in connection with FIG. 4 below. At the top of the member 66 there is shown a stop portion 74, which is seen in FIG. 3F and is formed with a slope of about forty-five degrees and with the lower extending lip providing the desired stop. This stop portion 74 is provided when the molding is being performed, but this is not to preclude other means such as a pin stop, which is not shown, or other means providing a desired one limit of travel. The back portion of member 66 is made sufficiently above the formed grooves to intergrally mold the stop portion 74. The lower portion of the member 66 is shown with a boss and shaped aperture for the sleeve which receives a connector assembly 41 described above. For the convenience of identification and using the identification of FIG. 2A, this member 66 has a boss 43, bore 44, reduced diameter bore 45 and a shallow counterbore 48 to the right of this bore 45. This shallow counterbore may be formed with or without flats 61a or as an alternate construction with small triangular inward-extending small ribs, not shown. This shallow counterbore is made so as to removably retain the flange end 56 of sleeve 55 as in FIG. 2C described above. The boss 43 is made of a determined extent or length so that the face 49 provides the limiting stop for the inward movement of the assembled connector.

In FIG. 3A, the front view of member 66 is shown. In FIG. 3B, a sectional side view taken on the line 3B—3B is illustrative of the depicted construction, and in FIG. 3C is illustrated the side view of this member. FIG. 3D shows a very fragmentary and enlarged view of a proposed and typical stop provided in the groove. FIG. 3E shows a view of the member 66 as taken on the line 3E—3E, and FIG. 3F shows a small fragmentary view of a molded protrusion forming and providing a suggested stop.

In FIGS. 3G, 3H and 3I, a plate-like member, generally identified as 76, is contemplated to be of molded plastic and has a T-shape, with both the wider and narrower portions sized to be a slide fit in the grooves 70 and 71 of member 66. It is, of course, noted that the narrower portion may be made so as to not be retained by the grooves. Preferably, the narrower portions are sized to slide by the inner edges of the stops 72 and 73 which are made less than the full depth of the grooves 70 and 71 for this purpose. The depth of the grooves and the stops as well as the width of the smaller portion of the T-shaped is a matter of design. Without or without retaining engagement, outwardly-extending shoulder portions 78 and 79 are disposed to engage the stop portions 72 and 73 of the grooved member 66. When the shoulder portions 78 and 79 are brought to and in engagement with stop portions 72 and 73, the axis of the upper bore in plate 76 is brought into coincidence with bore 44, reduced diameter bore 45 and shallow counterbore 48 in hub 43 of retaining member 66.

This upper boss and bore for the purpose of identification will apply the same numerals as used in FIGS. 2H and 2I discussed above. Plate member 76 has two boss portions and this upper boss is identified as 62, with a through bore 63 sized to removably retain a connector half 30. The flange 31 of a connector 30 is removably retained in the shallow counterbore 64 formed in this boss portion 62. This boss is only long enough to provide a guide and retainer for the connector half 30 as and when mounted therein.

The lower boss 52 provided in the lower portion of the T-shape is formed with a through bore 54 and counterbore 53 for the movement of the sleeve flange 48. The length or extent of this boss 52 is a matter of selection, but within the discussed limits of FIGS. 2C through 2G. In the illustration of FIGS. 2A through 2I, there is a small spacing therebetween, but it is proposed to make this space with a sliding seal. It is proposed that a window-frame type seal be formed on the facing and sliding surface of plate member 76. As shown, a border portion and a mid and transverse portion, generally identified as 80, provide a seal portion which is only a few thousandths of an inch in thickness, but in a projecting manner provide a sliding seal when manipulation is made. This seal prevents unwanted air from the outside from entry or access. Rather than a seal means formed by molding, it is also contemplated that a separate die-cut sheet member be attached to the T-shaped plate member or a seal could be formed by molding on the member 66 or attached to the inner face of this member. Except as a provision for a seal during manipulation, the shape and type of seal is a matter of selection. Alternate sealing means may be provided by making the area around the apertures extended either by molding or added adhered sealing portions.

Aperture 63, which extends through boss 62, is sized to releaseably retain connector half 30, depicted in FIG. 1F above, and connected by influent conductor 35 to a supply bag, not shown. The flange 31 of connector 30 is seated in a counterbore or recess which is sized and shallow enough to just retain this connector half without the forward or protruding end of the connector 30 coming in way of the other sliding member 66. Before assembly of members 66 and 76, the unused and sterile connector 30 is mounted into the top boss 62, with the bore 63 retaining said connector and with the flange 31 retained in shallow counterbore 64. As and when mounted, the flexible conductor 35 is connected to the supply bag, not shown, at a determined step in the assembly procedure. A sleeve 55 is mounted in bore 54 in boss 52. The counterbore 53 is sufficient in depth for the insertion of the sleeve sufficiently to avoid interference problems with assembly.

OPERATION OF SLIDE DEVICE AS IN FIGS. 4A THROUGH 4H

In FIG. 4A, there is illustrated the proposed assembly procedure for the sliding apparatus for making a sterile transfer and connection. An influent connector half, generally identified as 30, is placed with the flange 31 seated in counterbore 64 (FIG. 3G) in T-shaped member 76. The reducer diameter portion 32 and the knurled portion 33 are mounted in bore 63, with the tubular connector 35 extending to and connected to the dialysis solution bag (not shown). Also mounted in the T-shaped member and in the lower boss 52 is sleeve 55 mounted in bore 54 and is moved rightward so that the T-shaped member 76 may be inserted into the grooves 70 and 71 of member 60 without the sleeve 55 impeding in the assembling or coming in way of the mating member 66. The stop shoulder 74 is not intended to impede the mounting of member 76 within the grooves 70 and 71 of member 66. When slid into retaining condition, the slide member 76 is moved upwardly to the stop 74 whereat sleeve 55 may be moved to bring flange 56 into the shallow counterbore 48 in member 66. When brought to the position and condition of FIG. 4B, this connector is brought sufficiently leftwardly that the flange 56 is mounted in shallow counterbore 48 which was explained above in discussing FIG. 2C.

In FIG. 4C, the device of FIG. 4B is repeated, but with assembled connector 41 as indicated by the arrow. The approaching assembled device is now used to receive the connector body 16 slideable in bore 44 (FIG. 3C) in boss 43. An arrow indicating direction of movement is shown for the assembled connector halves 41. The sleeve placement corresponds to FIG. 2C above.

In FIG. 4D, the connector body 16 is shown as entering the bore 44 in boss 43 and the grommet closed end 40 of tubing 35 has not appeared and is not seen in bushing 55. This corresponds to the showing of FIG. 2D above.

In FIG. 4E, the connector assembly 41 has been inserted fully into sleeve 55 and the grommet 40 is visible. The sleeve 55 is now rotated, as indicated by the arrow, to break and separate the connector halves. After separation is completed by the indicated rotating motion, the connector halves correspond to the position depicted in FIG. 2F, but as the connector 30 must be moved from in way of any interference the sleeve 55 and connector half 30 are further moved to the right as indicated by the phantom line. This corresponds to the arrangement as seen in FIG. 2G. This movement and bringing the stops into contact bring the sterile influent connector half 30 into axial coincidence with the transferred effluent connector half 15 of FIG. 1E and bores in boss 43.

In FIG. 4F, the arrow indicates that a transfer motion has been made and achieved. The T-shaped member 76 has been moved downwardly so that the stop shoulders or portions 78 and 79 are against stops 72 and 73 at the bottom of the grooves. This establishes the other limit of movement of member 76. This corresponds to the position depicted in FIG. 2H, and the patient is ready to grasp the influent connector half 30 which is connected by tubing 35 to the fluid supply. This connector half is in sterile condition. The connector 30 and sleeve 55 in boss 52 may be pushed leftwardly from this boss and discarded if desired.

In FIG. 4G, the sliding transfer device is shown with arrows indicating manipulation of connector 30 and pushing effluent connector 15 to the stop and retaining this portion against turning. The axis of the bore 63 in boss 62 is in coaxial alignment with bore 45 in boss 43. Flutes 34 of the connector 30 or the knurled portion 33 are grasped and rotated to provide the securing of the threaded luer lock. This rotary action will cause the threaded wings 20a and 20b to enter and move into the threads 36 in the influent connector. The tapered portion 37 is caused to seat in socket 23 to effect a primary fluid-tight seal. A secondary and an insurance seal is provided by the resilient washer 25 as it is squeezed slightly at the end of the locking twist.

Figure 4H:
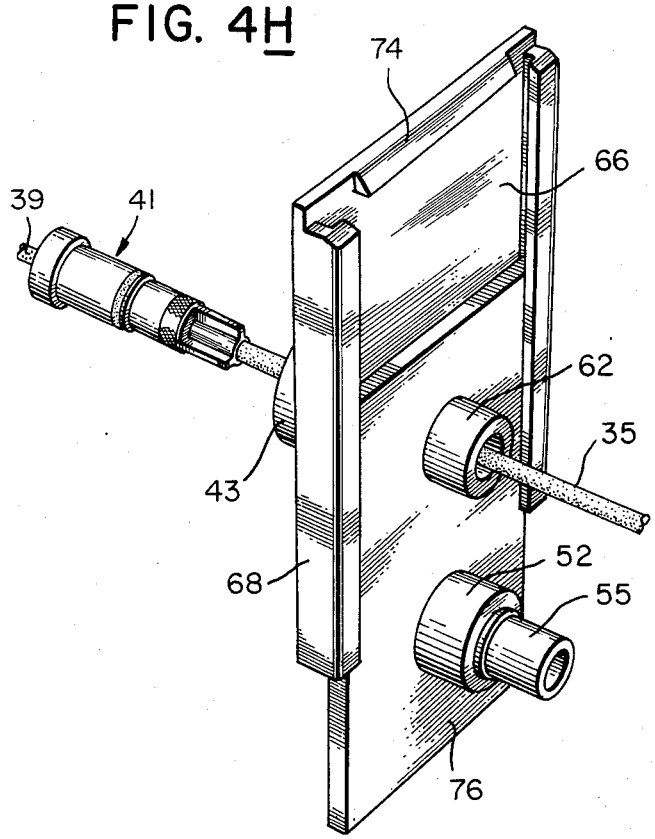

In FIG. 4H, the now-secured connector 41 is shown as moved from the sliding connector device, with tubing 39 extending to the patient and fluid from the supply bag, now shown, fed through tubing conductor 35 to the patient. This slide transfer device is allowed to remain on this conductor extent until the treatment is concluded whereat tubing 35 is cut and a grommet 40 is applied and the transfer device just used is removed and discarded.

It is to be noted that when the device has been manipulated to the position and condition of FIG. 4H, the sleeve 55 and the now-contaminated half connector 30 that is within the sleeve at FIG. 4G and is disconnected are now surplus. The sleeve 55 and the influent connector 30, the tubular conductor 35 and grommet 40 may be removed leftwardly and discarded if desired. The slide action providing the transfer actuation of FIG. 4F is not intended to affect the desired seal of the connector halves before and during transfer. No matter the configuration of the seal, it is important that exclusion of outside and contaminated air be achieved and maintained.

ALTERNATE SLEEVE CONSTRUCTION OF FIGS. 5A AND 5B

Figure 5A:
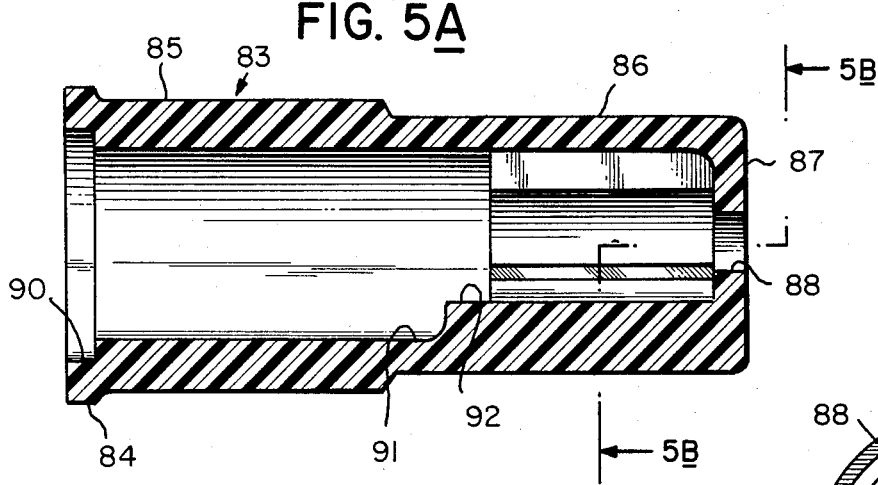
FIGS. 5A and 5B represent a sectional side view of an alternate sleeve construction and particularly for a rotary connection device.
Figure 5B:
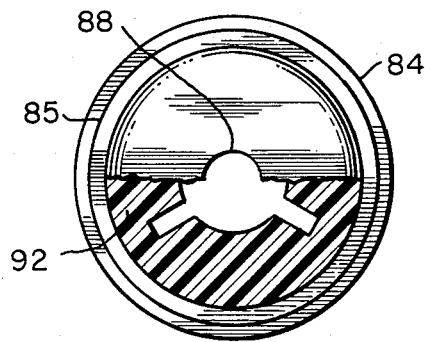

In FIGS. 5A and 5B, there is depicted an alternate sleeve that may be used in both transfer devices. This sleeve will be illustrated in the rotary transfer device shown in FIGS. 7A through 7F. The discernible difference in this sleeve and the sleeve 55 in FIG. 2A is that this sleeve, identified as 83, has a partially closed distal end. This sleeve 83 has a flange stop portion 84 and an intermediate diameter portion 85. As shown, this sleeve 83 has a reduced diameter 86 which terminates with an end wall 87. This end wall portion 87 has a through aperture 88 which is sized to freely pass the tubular conductor 35 identified above. As a grommet 40 may also be utilized for closing the cut tubing, the aperture 88 is contemplated as sufficiently large for this.

This sleeve 83 is contemplated to removably retain the assembled connector 41 as in FIG. 1I. For this purpose, this sleeve 83 is formed with a short inner bore 90 which is sized to removably retain the locating stop ring or flange 31 of the influent connector half 30. To the right is an inner diameter extent 91 sized to accept and retain the diameter portions 32 and 33 of this influent connector. A former recess 92 is contoured and shaped to receive and retain flutes 34 on this same connector half where and when flutes are provided. Still further to the right is the end portion 87 in which aperture 88 is formed. In function and use, this sleeve depiction is adapted to removably receive and retain the influent connector half and to be adapted for removable and rotative movement in the boss provided in one of the movable halves of the connector device.

EMBODIMENT OF FIGS. 6A, 6B AND 6C

Figure 6A:
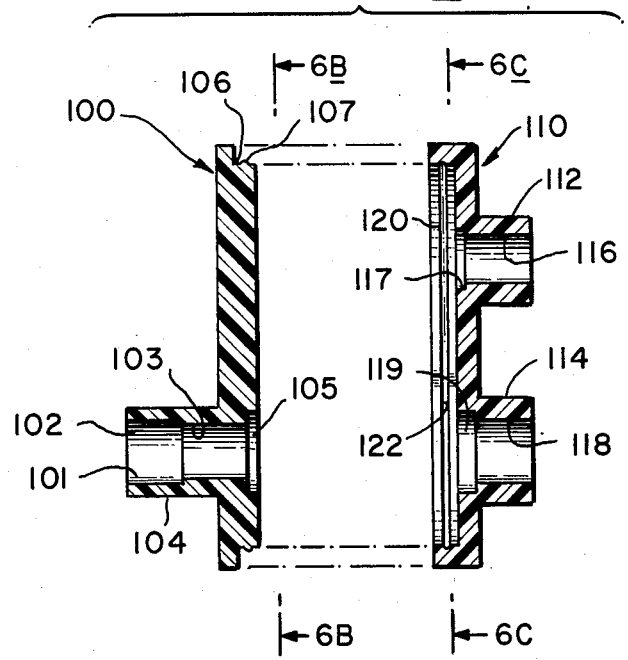
FIGS. 6A, 6B and 6C represent section side and face views of the members that constitute the rotary connector device.

Depicted in FIGS. 6A, B and C is the transfer device adapted for rotary manipulation. As depicted, the transfer half with two boss portions has a very shallow recess which is contemplated to bring the inner surfaces into substantially surface engagement, but it is also realized that greater interior space may be provided if desired and such greater spacing is contemplated. If an interior spacing is provided, limiting stops to establish the exact positioning of the members may be provided within this interior.

As shown in FIG. 6A, a disc, generally identified as 100, is formed with a bore 101 extending inwardly from a stop end 102. This bore 101 proceeds to a reduced diameter bore 103 formed in boss 104 extending from this disc 100. A counterbore 105 is formed to accept and retain the flange end of sleeve 55 or 83. A stop shoulder 102 is adapted to a corresponding stop 22 on connector 15 as seen in FIG. 1I. A counterbore 105 is also formed in this disc and the axis is in coincidence with bores 101 and 103. The outer periphery of disc 100 is formed with a reduced diameter portion 106 on which or in which is formed a peripheral projecting ring portion 107. A stop lug 108 is formed on the outer extent of the disc 100.

A mating cup-shaped member, generally identified as 110, is formed with two bosses 112 and 114. Boss 112 has a through bore 116 with a shallow counterbore 117. This bore and counterbore are sized and adapted to slideably retain the connector 30 as described in connection with FIG. 1F above. Boss 114 has a through bore 118 and counterbore 119 which are sized to removably retain the sleeve 55 or 83 as described above. The mid-diameter of these sleeves is usually a snug slide fit, but it is realized that it may be desired that the sleeve be made with a taper to provide a locking fit when the sleeve is moved into seating condition. The interior of this cup-shaped member 110 is identified as 120 and has a groove 122 sized and adapted to receive the ring portion 107 of disc member 100. A stop lug 124 is also formed on this member 110 and is spaced and positioned to engage the stop lug 108 on the disc cover member 100 when and as relative rotating motion has been achieved.

Figure 6B:
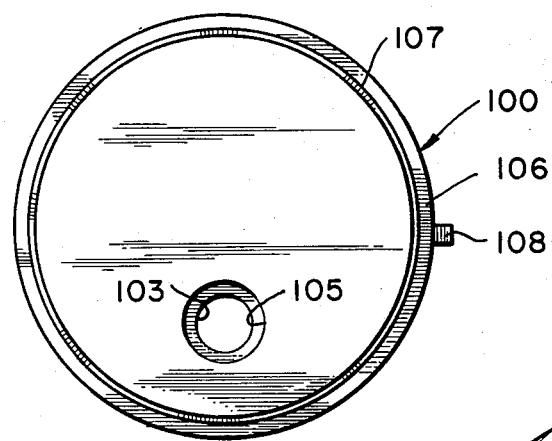

In FIG. 6B, there is depicted a face view of the disc member 100 to illustrate the providing of a stop member 108 as an integrally-molded portion of said disc member. The positioning and configuration of this stop is a matter of choice as the face of this stop need engage a face of the stop lug 124 as provided on the member 110 to establish positive rotational alignment.

Figure 6C:
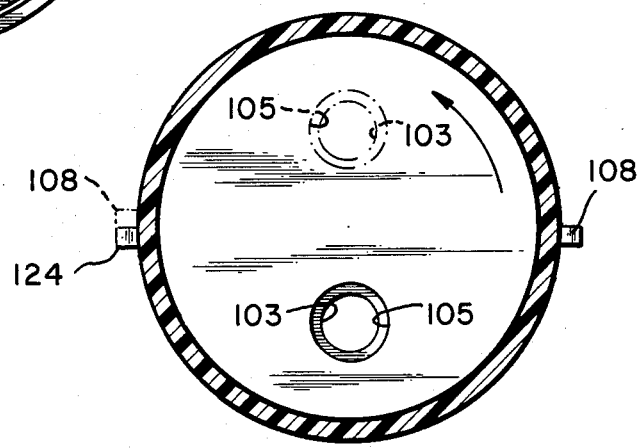

In FIG. 6C, the cup-shaped member 110 is shown as provided with a stop lug 124 which is molded as said member is molded. The face portions of the stop member 108 and lug 124 provide a rotational stop to insure alignment of the connector halves during the connection step. It is anticipated that sleeve 83 (FIG. 5A) or sleeve 55 (FIG. 4A) are used to enter counterbore 105 and establish the desired orientation, but other positive stop means may be provided such as an additional stop located about one hundred eighty degrees from stop 124.

It is contemplated that the ring portion 107 when seated in the groove 122 provide the desired exclusion of outside air, but it is also contemplated that if desired or required the inside portions of member 110 around apertures 118 have seal rings formed or additionally applied to the interior surface of this cup-shaped member 110. It is also to be noted that the ring 107 as formed on disc 100 and the groove 122 provided in member 110 may be reversed, and no patentable distinction is ascribed to this concept or position other than providing a rotatable and an easily assembled device. Modifications, particularly as to lug formation and position, are also contemplated.

ASSEMBLY AND USE OF ROTARY CONNECTOR AS IN FIGS. 7A THROUGH 7F

Figure 7A:
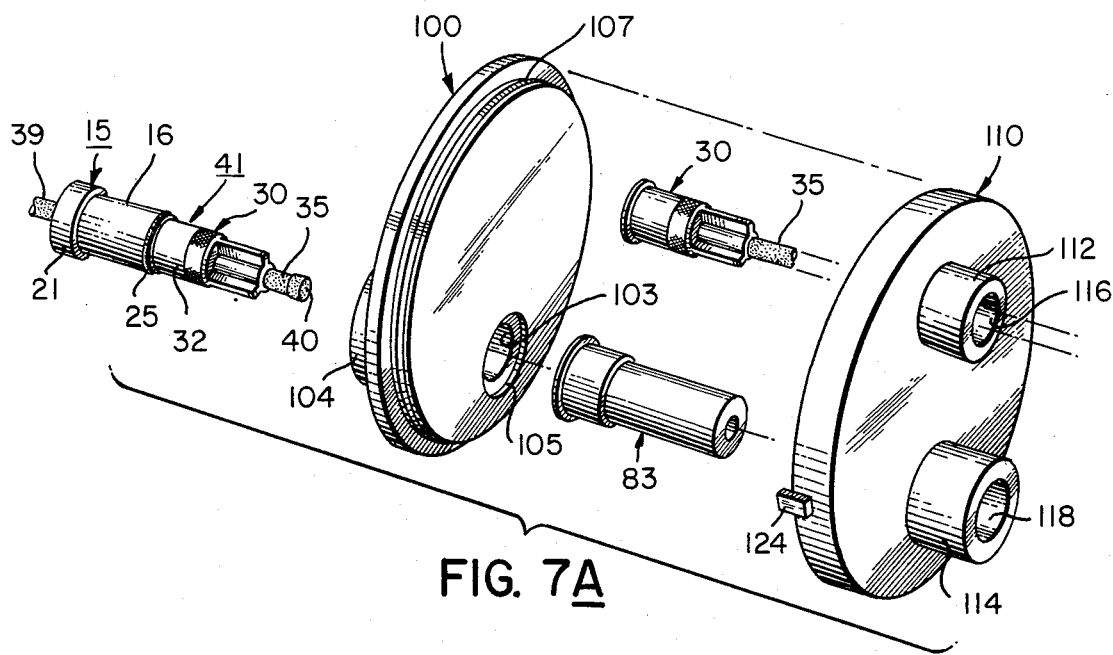
FIG. 7A represents an isometric exploded view of the several components that constitute the rotary transfer device.

This rotary connector, as shown in FIGS. 6A through C, is arrayed in an exploded view as in FIG. 7A to illustrate the relationship of the several components as desired and required. To the left of the rotary members is seen the assembled connector 41 as connected to the patient by a fluid conductor 39. The fluid conductor 35 and grommet 40 as described above pertain to the influent side of the connector. This grommet seals the tubing end. The disc member 100 is shown to the left of a new sterile connector, generally identified as 30, which connector body is slideably carried in bore 116 and counterbore 117 in boss portion 112. The fluid conductor 35 is depicted as stopping before rotary cup-shaped member 110, but in fact extends through bore 116 to the supply bag, not shown. Sleeve 83 (FIG. 5A) is depicted, but sleeve 55 or a like sleeve may be provided. This sleeve enters and is retained in the stepped bore 118 provided in boss 114.

Figure 7B:
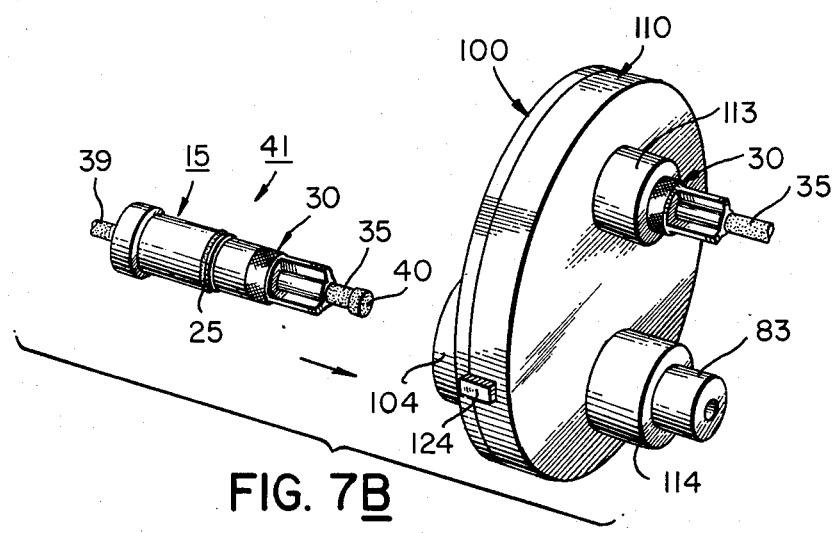
FIGS. 7B, 7C, 7D, 7E and 7F represent isometric views showing progressive stages of manipulation of the assembled members to effect disconnection, transfer, reconnection and moving the connector to a non-interfering position on the flexible conduit.

In FIG. 7B, the connector assembly 41 is shown and to the right thereof is the assembled rotary device. Sleeve 83 has been mounted within member 110 and sleeve 83 has flange portion 84 seated in counterbore 105. The influent connector half 30 is seen mounted in boss 112, with conductor 35 extending to the right to a supply bag, not shown.

Figure 7C:
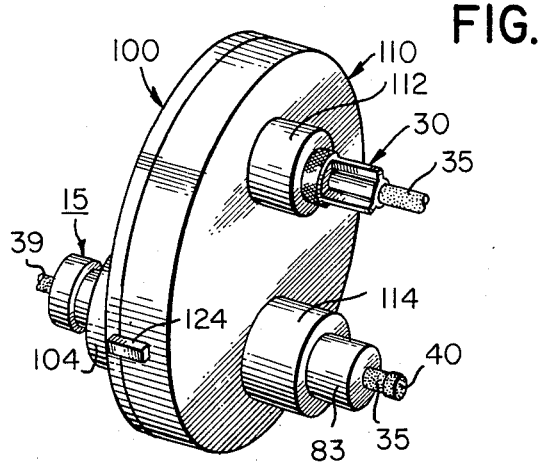

In FIG. 7C, the connector assembly 41 has been inserted into the sleeve 83 and the cut tubing 35 end and grommet 40 are seen. The sleeve 83 has not yet been dislodged from its mounted condition of FIG. 7B.

Figure 7D:
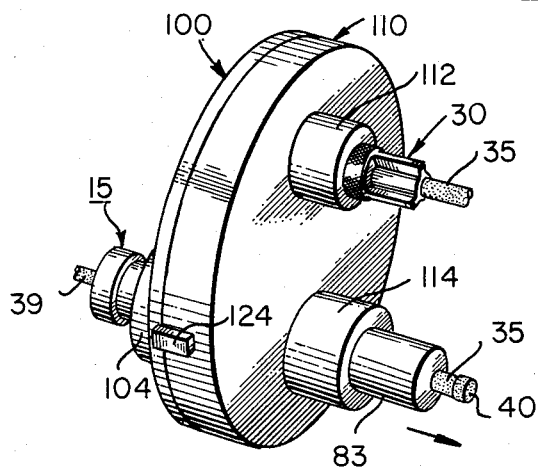

In FIG. 7D, the connector 41 has been moved rightward to the extent that sleeve 83 is at its rightward limit whereat manipulation of the sleeve and/or the effluent connector body are rotated in an unscrewing direction to effect separation of the effluent and influent halves. If and when the connection is with a slip fit luer lock, the rotation may be in either direction. When the connection is with a luer lock with threads, the unscrewing motion is counterclockwise as indicated by the arrow. After separation has been achieved, manipulation of the members as indicated by the arrow in FIG. 7E, is made.

Figure 7E:
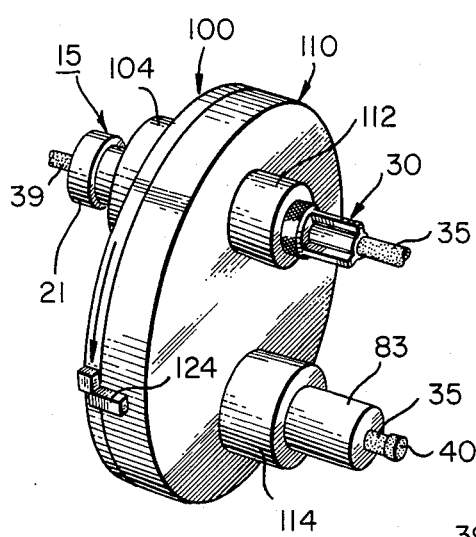

In FIG. 7E, there is shown a rotary motion for new alignment of the members 100 and 110. A positive stop is provided to establish the alignment of bores 102 and 116 as seen in FIG. 6A. A molded stop arrangement using stop lug 108 and stop 124 is shown, but other means may be provided and no patentable distinction is ascribed thereto. With alignment assured, the new influent connector half 30 is inserted into and secured in the effluent connector half 15. It is noted that the other and now-discarded or unwanted influent connector half 30 is in sleeve 83.

Figure 7F:
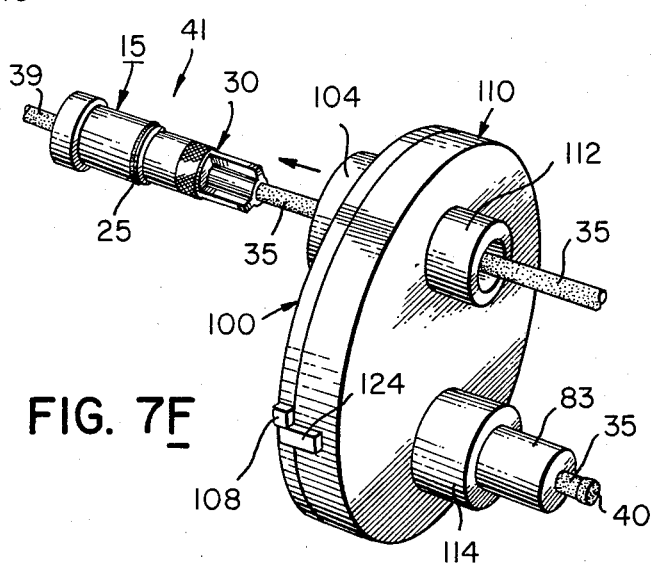

In FIG. 7F, the assembled connector is pushed leftwardly or the rotary device is moved rightwardly. The flexible tubing 35 is connected to tubing 39 and opening of the shut-off allows fluid to flow.

Figure 8A:
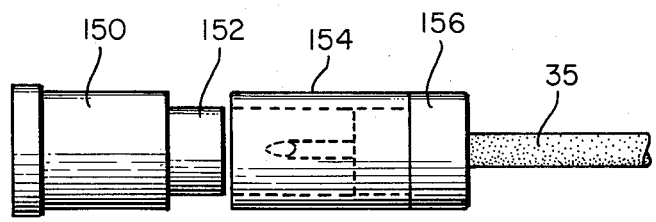
FIGS. 8A, 8B and 8C represent side and partly diagrammatic sectional views showing an alternate connector half.
Figure 8B:
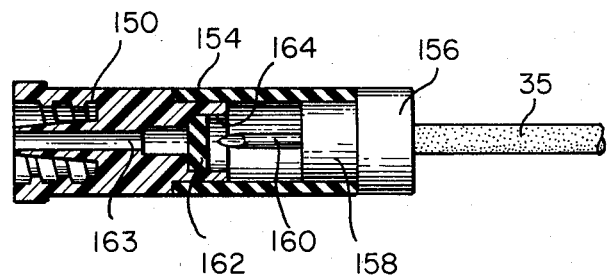
Figure 8C:
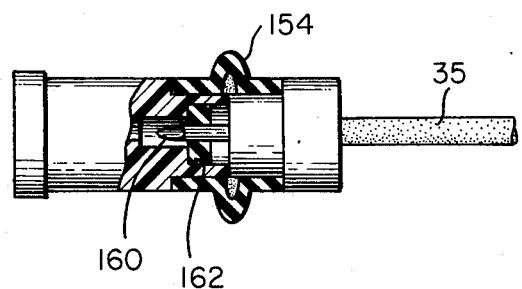

EMBODIMENT OF FIGS 8A, 8B and 8C

The influent connector may have a shut-off device made as part thereof so that connector mechanism can be shipped separately from the conductor 30 and bag without contamination of the connector device during transfer. There are many concepts, but illustrative of these is the concept shown in FIGS. 8A, 8B and 8C in which a luer lock connection is provided by and in body portion 150. Threads and a tapered inlet portion are similar to that shown in FIG. 1E. The right end of this body 150 is provided with a reduced diameter portion 152. A rubber tubular sleeve portion 154 is slideable on this reduced diameter 152 and is fluidtight. A right-end closure member 156 also has a left-end reduced diameter portion 158 in which is carried a needle 160. The closure member is adapted to receive and retain tubing 35 identified above.

In FIG. 8A, the connector device is shown in a side view before assembly is made.

In FIG. 8B, a sectional view of the connector is shown. A rubber disc 162 is secured within the cavity 164 provided by the sleeve 154 and the internal recess of the body 150. To the left of disc 162 is fluid-conducting path 163 leading to the influent connector 30 (FIG. 1F).

In FIG. 8C, the fluid-conducting pathway is established. Needle 160 has penetrated disc 162 and the rubber sleeve 154 has bulged to accommodate this forward (leftward) movement of closure member 156.

EMBODIMENT OF FIGS. 9A THROUGH 9E

Referring next, and finally, to an alternate shut-off device as provided in the FIGS. 9A through 9E, there is illustrated a body member 170 formed with an interior cavity 172 in which there are a plurality of passageways 173 formed by and with a square molding insert. The left end of the passageways 173 is formed with a taper with ribs 174 provided. The left end of this member 170 is formed with a diametrical recess 176 sized for a press fit of a tubular member 178. In this interior cavity 172 is placed a compression spring 179 sized to have the right end enter and urge cup-shaped member 180 rightward to and against tubular member 178.

In FIG. 9B, there is shown a cylindrical connector cap or actuator 182 made as a molded member. Flutes 184 may be provided and are indicated. A conduit path 186 is shown and is adapted to receive the influent conductor 35 (FIG. 1F). Into cavity 188 extends a tubular stem member 190 having a transverse relief 192 which provides a side discharge of fluid from the bag into the passageways 173. It is to be noted that the outer shell portion of this connector is formed with a bayonet connector groove 194. A pin or pins 196 is/are formed on the shank portion of member 170.

In FIG. 9C is shown the shut-off connector half portion, generally identified as 170, depicted and particularly showing the recess 176 with a frictionally or cemented tubular member 178 secured therein. This leaves the leftward portion with a square configuration forming passageways 173. The inner portion of tubular portion 178 exposes the cup-shaped member 180 which is moved when assembly is made.

In FIG. 9D, the fluid passageways 173 are shown with a square formation, but this is only a selected conformation as the configuration may be any selected shape. It is to be noted that the forward or left end of this passageway is tapered to meet passageway 198. Rib portions 174 (FIG. 9A) as provided shorten the required length of spring 179. As spring 179 is a compression spring with a hollow interior, the fluid also flows into passageway 173 to flow through the coils and into passageway 198.

In FIG. 9E, the bayonet lock is depicted. This connection device may have one or more pins 196 and a like number of retaining slots 194.

The use and operation of this cut-off connector anticipates that the left end of the connector 170 has luer locking means. The right end utilizes spring 179 to urge cup member 180 into engagement and shut-off of fluid when the member 180 engages the left face of tubular member 178. The actuator member 182 is brought to and is moved along the right end of member 170 with pin 196 entering slot 194 and then, with a rotating action of the cap 182, the cap is locked in place. With the pushing of cup member 180 to the left, fluid flows from transverse relief 192 into the plurality of passageways 173, thence into conduit 198.

It is to be noted that the luer lock arrangements may utilize a resilient seal to insure a fluid-tight connection. Luer lock or luer slip fittings have been used for many years for medical hook-up apparatus, but this is not to preclude other configurations as the essence of this invention is to provide an apparatus or device wherein a connector assembly can be disconnected in a protected environment and, while in this same environment, be moved to bring a new influent half into alignment with an effluent connector and effect a recoupling to provide a new sterile influent conducting path for fluids from a solution supply.

The above-shown embodiments have been illustrated in enlarged scale to more easily show the relationship of the several members. High production methods are contemplated and as the conducting tubing from the patient and supply bag is cut during periods of non-use, the movable connector device is in use for usually less than one hour. For dialysis hook-up, the manipulating assembly is or may be brought to the supply bag, leaving the connector and connected tubing relatively free or uninhibiting. The two embodiments shown and described are illustrative and changes within the scope of the concept and to accommodate production manufacturing apparatus are contemplated.

Terms such as "left," "right," "up," "down," "bottom," "top," "front," "back," "in," "out," "clockwise," "counterclockwise" and the like are applicable to the embodiments shown and described in conjunction with the drawings. These terms are merely for the purposes of description and do not necessarily apply to the position in which the movable connecting device may be constructed or used.

While two particular embodiments of the movable connection device have been shown and described, it is to be understood that the invention is not limited thereto and protection is sought to the broadest extent the prior art allows.

What is claimed is:

1. A connector apparatus having a retaining and guiding means which provides a movable transfer and alignment device adapted to receive and retain a separable connected fluid conductor having effluent and influent connector halves and, when said connection is brought to said transfer and alignment device, said effluent and influent connector halves are manipulated to effect separation, after which transfer is made and a positioning is effected to bring the effluent connector half into alignment with a new influent connector half and, with manipulation, the effluent and influent connector halves are connected to provide a fluid-tight conducting path, this connector transfer and alignment device including:
    (a) first and second movable members arrayed in substantially a face-to-face relationship and adapted for movement from one determined position to another selected position;
    (b) means for retaining said first and second movable members in said arrayed relationship during use;
    (c) a guideway in said first movable member, said guideway sized and adapted to receive and slideably retain a body portion of the effluent connector half;
    (d) a first guideway in said second movable member, said guideway sized and adapted to receive and rotatably and slideably retain a body portion of an influent connector half;
    (e) a second guideway in said second movable member, this guideway sized and contoured to receive a rotatable sleeve member, said sleeve member being of a tubular configuration and having a stop flange to limit longitudinal movement, the sleeve member having an interior sized and adapted to receive and retain a body of an influent connector half, and
    (f) stop means which provide two movement limits which determine said one determined position and said other selected position; whereby, in the first determined position the connected effluent and influent connector halves may be separated by manipulation and, while the halves are separated, the first and second movable members may be moved to the other selected position to align the first guideway of the second movable member, with a new influent connector therein, with the guideway in the first movable member and, through manipulation, connection of the now aligned connector halves may be achieved to establish a fluid flow path, and second movable members are moved so that the second guideway and sleeve containing an influent connector half are moved from in way of the now-separated effluent connector half in the guideway of the first movable member and this effluent connector half is repositioned so that said effluent connector half is aligned with the second guideway in the second movable member and the influent connector therein whereat, through manipulation, connection of the halves of the connector is achieved to establish a fluid flow path.

2. A connector apparatus, as in claim 1, in which the first and second movable members are adapted to be moved back and forth in a reciprocal path and manner and their inner surfaces are substantially contiguous.

3. A connector apparatus, as in claim 2, in which the first movable member is formed with parallel grooves in longitudinal edge portions and the second movable member has edge portions sized and shaped to slide and be retained by said grooved edge portions in said first movable member.

4. A connector apparatus, as in claim 3, in which the stop means includes at least one stop shoulder formed in at least one of said grooves and the second movable member has a T-shape, with the longitudinal edge portions sized to slide in the grooves of the first movable member, the offset provided by the T-shape providing a stop lip when and as it engages the at least one stop shoulder in the groove to establish one of the movement limits.

5. A connector apparatus, as in claim 4, in which the second movement limit is provided by a stop lip or protrusion provided by or on the first movable member.

6. A connector apparatus, as in claim 2, in which the connector halves have a compatibly-formed luer lock construction and configuration.

7. A connector apparatus, as in claim 6, in which the effluent connector half is fluid-connected to the patient by a flexible conduit also secured to the effluent connector half, and the influent connector half carried in the first guideway of the second movable member is connected by a flexible conductor to a fluid supply.

8. A connector apparatus, as in claim 7, in which at least one of the connector halves has a resilient washer at the engaging faces so as to provide an additional seal of the fluid pathway.

9. A connector apparatus, as in claim 8, in which a resilient washer is carried on a shoulder provided on a body portion of the effluent connector half.

10. A connector apparatus, as in claim 1, in which the guideway in the first movable member is a boss whose outer end is finished to provide a stop and the effluent connector half has an enlarged portion with a stop face disposed to engage the outer end of said boss.

11. A connector apparatus, as in claim 10, in which the influent connector half is formed with a shoulder portion at that end selectively in engagement with the resilient washer, this diameter of the shoulder portion sized to pass through the guideway in the first movable member.

12. A connector apparatus, as in claim 11, in which the sleeve is formed with an exterior and outwardly-extending shoulder of limited length and extent, said second guideway in said second movable member formed with a reduced diameter sufficiently long and in diameter to rotatably retain the sleeve substantially in a position which maintains the face of the sleeve, the face of the influent connector half and the movable member in a common plane.

13. A connector apparatus, as in claim 12, in which the sleeve is formed with an internal counterbore sized to receive and retain the shoulder portion on the influent connector half.

14. A connector apparatus, as in claim 13, in which the influent connector half is formed with a plurality of flutes at the distal end thereof and with said sleeve formed with a compatible portion disposed to receive and engage the flutes as the influent connector half is removably inserted therein.

15. A connector apparatus, as in claim 12, in which the guideway in the first movable member is formed with a shallow counterbore extending from that face surface opposite the second movable member, this counterbore sized to removably retain the outwardly-extending shoulder of said sleeve.

16. A connector apparatus as in claim 5, in which the influent connector half further includes a shut-off valve means that provides selective fluid flow through the influent connector half.

17. A connector apparatus, as in claim 16, in which the shut-off valve includes a rubber or rubber like disc that may be punctured by a needle to establish a fluid flow path and a resilient tubular shield that surrounds and extends rearwardly from the disc.

18. A connector apparatus, as in claim 16, in which the shut-off valve includes a check valve having a resilient cup-shaped member slideably urged by a spring into a shut-off condition, said check valve being openable in response to a tubular extension engaging and moving the cup-shaped member into a fluid-bypass condition.

19. A connector apparatus, as in claim 18, in which the telescoping portions are retained in a mating position by a pin and bayonet groove, with the pin in one valve portion and the bayonet groove in the other portion.

20. A connector apparatus, as in claim 1, in which between the first and second movable members there is provided a sealing means to provide exclusion of outside air to the guideways during use and manipulation.

21. A connector apparatus, as in claim 1, in which the effluent and influent connector halves further include fast thread connecting means.

22. A connector apparatus, as in claim 21, in which a seal is formed between the first and second movable members by at least one raised surface formed on the second movable member during molding.

23. A connector apparatus, as in claim 22, in which there are two raised surfaces, one surrounding each of the first and second guideway openings.

24. A connector apparatus, as in claim 1, in which the first and second members are substantially circular in shape and the transfer is with a rotating motion.

25. A connector apparatus, as in claim 24, in which the sleeve used therewith is formed with a partially-closed distal end which is sized to provide an aperture through which a severed length of flexible conductor may pass.

26. A connector apparatus, as in claim 25, in which the severed conductor is closed by an articulated and closed grommet.

27. A connector apparatus, as in claim 24, in which the means for retaining the first and second movable members is a ring integrally formed in the first movable member and a groove formed in said second movable member, the ring and groove adapted for a snap-in mounting of the two members to provide a face-to-face relationship.

28. A connector apparatus, as in claim 27, in which the first and second movable members are each provided with molded lugs so spaced that in one position the lugs come into engagement to establish the one determined position, bringing the first guideway in the second movable member into axial alignment with the guideway in the first movable member.

29. A connector apparatus, as in claim 28, in which the interior faces of the first and second rotary movable members are substantially contiguous.

30. A connector apparatus, as in claim 29, in which the connector halves have a compatibly-formed luer lock construction and configuration.

31. A connector apparatus, as in claim 30, in which the effluent connector half is fluid-connected to the patient by a flexible conduit also secured to the effluent connector half, and the influent connector half carried in the first guideway of the second movable member is connected by a flexible conductor to a fluid supply.

32. A connector apparatus, as in claim 31, in which at least one of the connector halves has a resilient washer at the engaging faces so as to provide an additional seal of the fluid pathway.

33. A connector apparatus, as in claim 31, in which a resilient washer is carried on a shoulder provided on a body portion of the effluent connector half.

34. A connector apparatus, as in claim 33, in which the guideway in the first movable member is a boss whose outer end is finished to provide a stop and the effluent connector half has an enlarged portion with a stop face disposed to engage the outer end of said boss.

35. A connector apparatus, as in claim 34, in which the influent connector half is formed with a shoulder portion at that end selectively in engagement with the resilient washer, this diameter of the shoulder portion sized to pass through the guideway in the first movable member.

36. A connector apparatus, as in claim 35, in which the sleeve is formed with an exterior and outwardly-extending shoulder of limited length and extent, said second guideway in said second movable member formed with a reduced diameter sufficiently long and in diameter to rotatably retain the sleeve substantially in a position which maintains the face of the sleeve, the face of the influent connector half and the movable member in a common plane.

37. A connector apparatus, as in claim 36, in which the sleeve is formed with an internal counterbore sized to receive and retain the shoulder portion on the influent connector half.

38. A connector apparatus, as in claim 37, in which the influent connector half is formed with a plurality of flutes at the distal end thereof and with said sleeve formed with a compatible portion disposed to receive and engage the flutes as the influent connector half is removably inserted therein.

39. A connector apparatus, as in claim 38, in which the guideway in the first movable member is formed with a shallow counterbore extending from that face surface opposite the second movable member, this counterbore sized to removably retain the outwardly-extending shoulder of said sleeve.

40. A connector apparatus, as in claim 29, in which the influent connector half further includes a shut-off valve means that provides selective fluid flow through the influent connector half.

41. A connector apparatus having a retaining and guiding means which provides a reciprocably movable transfer and alignment device adapted to receive and retain a separable connected fluid conductor having effluent and influent connector halves and, when connected halves in said connection are brought to said transfer and alignment device, said effluent and influent connector halves are manipulated to effect separation, after which transfer is made and a positioning is effected to bring the effluent connector half into alignment with a new influent connector half and, with manipulation, the effluent and said new influent connector halves are connected to provide a fluid-tight conducting path, this connector transfer and alignment device including:

(a) first and second movable members arrayed in substantially a face-to-face contiguous relationship and adapted for movement from a first determined stop position to a second determined stop position and with a sealing means provided between the facing surfaces;

(b) a groove formed in each side extent arrayed along each longitudinal side of the first movable member and with these grooves substantially alike and parallel and in the bottom of each of these grooves providing stop portions extending inwardly toward each other at least part way of the depth of the grooves, the second movable member being generally plate-like and having a T-shape and intermediate the side extents of the T-shape providing a shoulder forming a stop when and as these shoulders engage the stop portions in each groove, and a lip or shoulder carried by the first member and establishing a stop limit at the other extreme of movement when the second movable member comes in way of this lip or shoulder and with the wider portion of the second member slideable and retained in the grooves;

(c) a through guideway in said first movable member, said guideway sized and adapted to receive and slideably retain a body portion of the effluent connector half, this connector half having a cooperative connection means;

(d) a first guideway in said second movable member, said guideway sized and adapted to receive and rotatably and slideably retain a body portion of an influent connector half, this guideway having a shallow counterbore formed in and at the interior face of the second movable member and with the body portion of said influent connector half having a flange portion slideably and rotatably sized to be retained in the counterbore formed in this first guideway, this influent connector half having cooperative means for connection to the effluent connector half, and (e) a second guideway in said second movable member, this guideway sized and contoured to receive a rotatable sleeve member, said sleeve member being of a tubular configuration and having a stop flange to limit longitudinal movement, the sleeve member having an interior sized and adapted to receive and retain a body of an influent connector half; whereby, when the movable members are brought to a first determined position at the extreme of movement provided by the stop lip, the connected effluent and influent connector halves, including a sleeve member removably retained on said influent connector half, may be inserted through the guideway in the first movable member and, separated by manipulation and, when and while separated, the first and second movable members may then be moved so that, using the stop provided by the shoulder stops on this T-shaped second member and the stop portions provided in the grooves of the first movable member, said effluent connector half is aligned with the first guideway in the second movable member and the influent connector therein whereat, through manipulation, connection of the halves of the connector is achieved to establish a fluid flow path.

42. A method of separating a connector having two portions and, after separation of the connector portions, moving an effluent connector portion to and in alignment with another fluid-connected influent connector portion whereat said effluent and influent through connector portions are connected to provide a fluid-tight conducting path, this separation, transfer and connection including the method steps of:

(a) arranging first and second movable members in substantially a face-to-face relationship so that movement may be made from one determined stop position to another selected stop position;

(b) retaining said first and second movable members is said face-to-face relationship during use;

(c) forming and providing a guideway in said first movable member, said guideway sized and adapted to receive and slideably retain a body portion of the effluent connector half;

(d) forming and providing a first guideway in said second movable manner, said guideway sized and adapted to receive and rotatably and slideably retain a body portion of an influent connector half;

(e) forming and providing a second guideway in said second movable member, this guideway sized and contoured to receive a rotatable sleeve member being member, said sleeve of a tubular configuration and forming thereon a stop flange to limit longitudinal movement, the sleeve member having an interior sized and adapted to receive and retain a body of an influent connector half, and (f) forming stop means which provide two movement limits which determine said one determined stop position and other selected stop position; whereby, in the first determined stop position the connector effluent and influent connector halves are separated by manipulation and, while the halves are separated, the first and second movable members are moved to the other selected stop position to align the first guideway of the second movable member, with a new influent connector therein, with the guideway in the first movable member and, through manipulation, connection of the now aligned connector halves is achieved to establish a fluid flow path.

* * * * *